(12) United States Patent
Qadan

(10) Patent No.: US 9,821,018 B2
(45) Date of Patent: Nov. 21, 2017

(54) **COMPOSITION COMPRISING *RAPHANUS*, *THEOBROMA* AND *PASSIFLORA* FOR TREATING OPIOID AND ALCOHOL ABUSE**

(71) Applicant: ARABIAN GERMAN MEDICAL PRODUCTS CO. W.L.L., Manama Center (BH)

(72) Inventor: Fadi Qadan, Amman (JP)

(73) Assignee: Arabian German Medical Products Co. W.L.L, Manama Center (BH)

( * ) Notice: Subject to any disclaimer, the term of this patent is extended or adjusted under 35 U.S.C. 154(b) by 0 days.

(21) Appl. No.: 14/653,900

(22) PCT Filed: Dec. 20, 2013

(86) PCT No.: PCT/IB2013/061217
§ 371 (c)(1),
(2) Date: Jun. 19, 2015

(87) PCT Pub. No.: WO2014/097259
PCT Pub. Date: Jun. 26, 2014

(65) Prior Publication Data
US 2015/0320815 A1 Nov. 12, 2015

(30) Foreign Application Priority Data
Dec. 20, 2012 (EP) ..................... 12198729

(51) Int. Cl.
*A61K 36/00* (2006.01)
*A61K 36/185* (2006.01)
*A61K 47/44* (2017.01)
*A61K 36/88* (2006.01)
*A61K 36/31* (2006.01)

(52) U.S. Cl.
CPC ............ *A61K 36/185* (2013.01); *A61K 36/31* (2013.01); *A61K 36/88* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 2004/0037792 A1 | 2/2004 | Hiramoto et al. | |
| 2005/0100622 A1* | 5/2005 | Nair | A23L 1/3002 424/777 |
| 2005/0181101 A1* | 8/2005 | Harada | C09B 61/00 426/250 |
| 2010/0297230 A1 | 11/2010 | Fletcher | |
| 2011/0280977 A1 | 11/2011 | Park et al. | |
| 2013/0165531 A1* | 6/2013 | Shi | A23L 1/2751 514/769 |

FOREIGN PATENT DOCUMENTS

| | | | |
|---|---|---|---|
| CN | 101062328 | 10/2007 | |
| CN | 102784351 | 11/2012 | |
| FR | EP 1537789 A1 * | 6/2005 | ........... A23L 1/3002 |
| FR | 2885300 | 11/2006 | |
| JP | 2000083654 | 3/2000 | |
| JP | 2010001282 | 1/2010 | |
| JP | 2010-526036 A | 7/2010 | |
| JP | 2011-528321 A | 11/2011 | |
| RU | 2151610 | 6/2000 | |
| WO | 2002/066041 A1 | 8/2002 | |
| WO | 2008/131911 A1 | 11/2008 | |
| WO | 2008131911 | 11/2008 | |
| WO | 2009/155585 A1 | 12/2009 | |
| WO | 2011025120 | 3/2011 | |

OTHER PUBLICATIONS

Billot, Anthocyanic pigments of *Passiflora quadrangulari* flowers. Phytochemistry (Elsevier) (1974), 13(12), 2886.*
Hajhashemi et al, Black cumin seed essential oil, as a potent analgesic and antiinflammatory drug. Phytotherapy research: PTR, (Mar. 2004) vol. 18, No. 3, pp. 195-199.*
Dhawan et al, Evaluation of Central Nervous System Effects of *Passiflora incarnata* in Experimental Animals. Pharmaceutical biology (2003), vol. 41, No. 2, pp. 87-91.*
International Search Report for corresponding PCT/IB2013/061217 dated Apr. 16, 2014.
Khawaja, Owais, J. Michael Gaziano, and Luc Djoussé. "Chocolate and coronary heart disease: a systematic review" Current atherosclerosis reports (2011) 13(6): 447-452.
Speroni, E., et al. "Sedative effects of crude extract of *Passiflora incarnata* after oral administration" Phytotherapy Research (1996) 10:S92-S94.
Speroni, E., and A. Minghetti, "Neuropharmacological activity of extracts from *Passiflora incarnata*" Planta Med. (1988) 54:488-491.
Vargas, R. et al., "Antiurolithiatic activity of Raphanus sativus aqueous extract on rats" Journal of Ethnopharmacology (1999) 68:335-338.
Ding et al., Nutr Metab (Lond), 3:2 (2006): Chocolate and Prevention of Cardiovascular Disease: A Systematic Review.
di Tomaso et al., Nature, 382, 677-678 (1996): Brain cannabinoids in chocolate.
Macht M. and Mueller J, J Nery Ment Dis., 195(12):1024-6 (2007): Interactive effects of emotional and restrained aating on responses to chocolate and affect.

(Continued)

*Primary Examiner* — Qiuwen Mi
(74) *Attorney, Agent, or Firm* — DT Ward, PC; Donna T. Ward; Lingyun Jia

(57) ABSTRACT

The present invention relates to a composition comprising a) an extract of a plant belonging to the genus *Raphanus*, wherein said extract is obtainable or obtained by extracting at least the air roots, seeds and/or bulbs with a hydrophilic, medium-polar and/or lipophilic solvent; b) an extract of a plant belonging to the genus *Theobroma*, wherein said extract is obtainable or obtained by extracting at least the fruit with a hydrophilic and/or medium-polar solvent, and c) an extract of a plant belonging to the genus *Passiflora*, wherein said extract is obtainable or obtained by extracting at least the flower with a hydrophilic, medium-polar and/or lipophilic solvent, its use in treating opioid abuse, opioid dependency, alcohol dependency and/or alcohol abuse and/or for use in treating the symptoms of opioid and/or alcohol withdrawal, and a method for its production.

14 Claims, 4 Drawing Sheets

(56) References Cited

OTHER PUBLICATIONS

Figure 1:
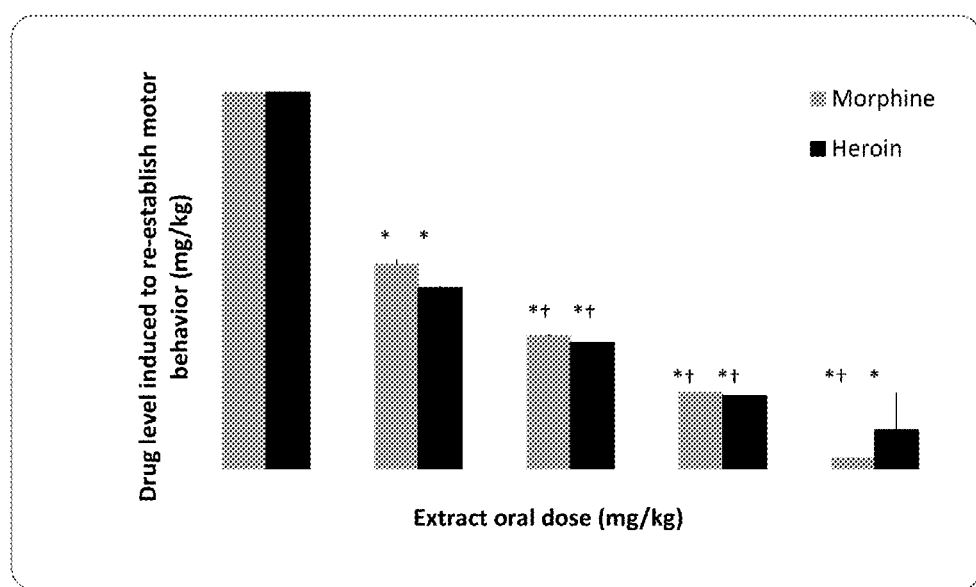

Ramos-Romero S., et al., Br J Nutr, 107(3):378-87 (2012): Effect of cocoa-enriched diets on lymphocytes involved in adjuvant arthritis in rats.

Andújar et al., Oxidative Medicine and Cellular Longevity, vol. 2012: 1-23 (2012): Cocoa polyphenols and their potential benefits for human health.

Sakagami H. et al., In Vivo, 25(2):229-36 (2011): Anti-HIV and immunomodulation activities of cacao mass lignin-carbohydrate complex.

Gutierrez R.M. and Perez R.L., Scientific World Journal, 4: 811-837 (2004): Raphanus sativus (Radish): their chemistry and biology.

Beevi et al., Plant Foods Hum Nutr., 65(1):8-17 (2010): Polyphenolics profile, antioxidant and radical scavenging activity of leaves and stem of *Raphanus sativus* L.

Beevi et al., Nat Prod Res., 26(6):557-63 (2012): Polyphenolics profile and antioxidant properties of *Raphanus sativus* L.

Seevi et al., Plant Foods Hum Nutr., 65(3):200-9 (2010): Hexane extract of *Raphanus sativus* L. roots inhibits cell proliferation and induces apoptosis in human cancer cells by modulating genes related to apoptotic pathway.

Scholl et al., J Food Sci., 76(3):C504-11 (2011): Raphasatin is a more potent inducer of the detoxification enzymes than its degradation products.

Shukla et al, Pharm Biol., 49(1):32-7 (2011): Antidiabetic effect of *Raphanus sativus* root juice.

He et al., Int J Mol Sci., 13(10):13065-78 (2012): Supercritical carbon dioxide extraction of flavonoids from pomelo (*Citrus grandis* (L.) Osbeck) peel and their antioxidant activity.

Dhawan et al., J Ethnopharmacol.;94:1-23 (2004): Passiflora: a review update.

Dhawan et al., J Pharm Pharmaceut Sci., 6(2):215-222 (2003): Attenuation of benzodiazepine dependence in mice by a tri-substituted benzoflavone moiety of *Passiflora incarnata* Linneaus: A non-habit forming anxiolytic.

Nassiri-Asl et al., BMC Complement Altera Med., 8;7:26 (2007); Anticonvulsant effects of aerial parts of *Passiflora incarnata* extract in mice: involvement of benzodiazepine and opioid receptors.

Nassiri-Asl et al., Progess in Neuro-Psychopharmacology and Biological Psychiatry, 32:989-993 (2008): Anticonvulsive effects of intracerebroventricular administration of rutin in rats.

Movafegh et al., Anesth Analg., 106(6):1728-32 (2008): Preoperative oral *Passiflora incarnata* reduces anxiety in ambulatory surgery patients: a double-blind, placebo-controlled study.

Akhondzadeh et al., J Clin Pharm Ther., 26(5):363-7 (2001) Passionflower in the treatment of generalized anxiety: a pilot double-blind randomized controlled trial with oxazepam.

Akhondzadeh et al., J Clin Pharm Ther., 26(5):369-73 (2001): Passionflower in the treatment of opiates withdrawal: a double-blind randomized controlled trial.

Singh et al., Journal of Ethnopharmacology, vol. 139, issue 1, p. 273-279 (2012): Dual protective effect of Passiflora incamata in epilepsy and associated post-ictal depression.

Srivastava et al., Pharmacogn Rev., 4(8):200-8 (2010): *Crocus sativus* L.: A comprehensive review (http://www.ncbi.nlm.nih.gov/pmc/articles/PMC32499221?report=printable).

Fatehi et al., J Ethnopharmacology, 84:199-203 (2003): Effects of Petals Extracts of Saffron on Rat Blood Pressure and on Responses Induced by Electrical Field Stimulation in the Rat Isolated Vas Deferens and Guinea—Pigileum.

Hosseinzadeh et al., Fitoterapia, 77:446-8 (2006); Evaluation of the antitussive effect of stigma and petals of saffron (*Crocus sativus*) and its components, safranal and crocin in guinea pigs.

Pitsikas et al., Phytomedicine, 15:1135-9 (2008): Effects of the active constituents of *Crocus sativus* L., crocins, in an animal model of anxiety.

Nemati et al., Phytomedicine, 15:1038-45 (2008); Stimulatory effect of *Crocus sativus* (saffron) on beta2-adrenoceptors of guinea pig tracheal chains.

Moshiri et al., Phytomedicine, 13:607-11 (2006): *Crocus sativus* L. (petal) in the treatment of mild-to-moderate lepression: a double-blind, randomized and placebo-controlled trial.

Sugiura et al., Phytother Res., 9:100-4 (1995): Crocin Improves the Ethanol-induced Impairment of Learning Behaviors of Mice in Passive Avoidance Tasks.

Xuan B.,J Ocul Pharmacol Ther, 15:143-52 (1999); Effects of crocin analogs on ocular blood flow and retinal function.

Ghoshooni et al., Pak J Biol Sci., 14(20):939-44 (2011): Saffron (*Crocus sativus*) ethanolic extract and its constituent, safranal, inhibits morphine-induced place preference in mice.

European Patent Office Communication pursuant to Article 94(3) EPC, dated Mar. 9, 2017, issued in counterpart European Patent Application No. 13 836 199.3.

Dhawan, K. et al., "Reversal of Morphine Tolerance and Dependence by Passiflora incarnata—A Traditional Medicine to Combat Morphine Addiction" (2002) Pharmaceutical Biology 40(8): 576-580.

Hoshiwa, K., Duke Green Pharmacy Health Industry News Co., Ltd., Oct. 15, 2001, pp. 171-172.

Encyclopedia of Traditional Chinese Medicine, vol. 3, May 1998, First Edition, Third Printing, pp. 1574-1575.

Office Action dated Sep. 4, 2017 in co-pending Japanese application No. 2015-548872, entitled: Composition Comprising Raphanus, Theobroma and Passiflora for Treating Opioid and Alcohol Abuse.

Translation—Office Action dated Sep. 4, 2017 in co-pending Japanese application No. 2015-548872, entitled: Composition Comprising Raphanus, Theobroma and Passiflora for Treating Opioid and Alcohol Abuse.

* cited by examiner

COMPOSITION COMPRISING *RAPHANUS*, *THEOBROMA* AND *PASSIFLORA* FOR TREATING OPIOID AND ALCOHOL ABUSE

CROSS REFERENCE TO RELATED APPLICATIONS

This application is a 35 U.S.C. §371 U.S. National Stage Entry of International Application No. PCT/IB2013/061217 filed Dec. 20, 2013, which claims the benefit of priority of 12198729.1 filed Dec. 20, 2012 the content of each of which is incorporated herein by reference in their entirety.

The present invention relates to a composition comprising a) an extract of a plant belonging to the genus *Raphanus*, wherein said extract is obtainable or obtained by extracting at least the air roots, seeds and/or bulbs with a hydrophilic, medium-polar and/or lipophilic solvent; b) an extract of a plant belonging to the genus *Theobroma*, wherein said extract is obtainable or obtained by extracting at least the fruit with a hydrophilic and/or medium-polar solvent, and c) an extract of a plant belonging to the genus *Passiflora*, wherein said extract is obtainable or obtained by extracting at least the flower with a hydrophilic, medium-polar and/or lipophilic solvent, its use in treating opioid abuse, opioid dependency, alcohol dependency and/or alcohol abuse and/or for use in treating the symptoms of opioid and/or alcohol withdrawal, and a method for its production.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Opioid and alcohol abuse are complex illnesses characterized by intense and, at times, uncontrollable craving for the latter drugs, along with compulsive drug seeking and use that persists even in the face of devastating consequences. Addiction is a brain disease that affects multiple brain circuits, including those involved in reward and motivation, learning and memory, and inhibitory control over behavior. Because drug abuse and addiction have so many dimensions and disrupt so many aspects of an individual's life, treatment is not simple. The current practice to treat opioid and alcohol abuse includes medications to help in suppressing withdrawal symptoms during detoxification and to help reestablish normal brain function and to prevent relapse and diminish cravings. At present, methadone, buprenorphine and, for some individuals, naltrexone are medications for the treatment of opioid addiction. Acting on the same targets in the brain as heroin and morphine, methadone and buprenorphine suppress withdrawal symptoms and relieve cravings. Naltrexone works by blocking the effects of heroin or other opioids at their receptor sites and should only be used in patients who have already been detoxified. Because of compliance issues, naltrexone is not as widely used as the other medications. All medications help patients disengage from drug seeking and related criminal behavior and become more receptive to behavioral treatments.

Three medications have been FDA-approved for treating alcohol abuse: naltrexone, acamprosate, and disulfiram. A fourth, topiramate, is showing encouraging results in clinical trials. Naltrexone blocks opioid receptors that are involved in the rewarding effects of drinking and in the craving for alcohol. Acamprosate is thought to reduce symptoms of protracted withdrawal, such as insomnia, anxiety, restlessness, and dysphoria (an unpleasant or uncomfortable emotional state, such as depression, anxiety, or irritability). Disulfiram interferes with the degradation of alcohol, resulting in the accumulation of acetaldehyde, which, in turn, produces a very unpleasant reaction that includes flushing, nausea, and palpitations if the patient drinks alcohol. Compliance can be a problem, but among patients who are highly motivated, disulfiram can be very effective.

The technical problem underlying the present invention was to identify alternative and/or improved means and methods to treat opioid and alcohol abuse and symptoms of opioid and alcohol abuse.

The solution to this technical problem is achieved by providing the embodiments characterized in the claims.

Accordingly, the present invention relates in a first embodiment to a composition comprising a) an extract of a plant belonging to the genus *Raphanus*, wherein said extract is obtainable or obtained by extracting at least the air roots, seeds and/or bulbs with a hydrophilic, medium-polar and/or lipophilic solvent; and b) an extract of a plant belonging to the genus *Theobroma*, wherein said extract is obtainable or obtained by extracting at least the fruit with a hydrophilic and/or medium-polar solvent "Extracting" as used herein is meant to be a process of solubilising compounds that are contained in the plant material to be extracted and subsequent release of those compounds from said material. The released compounds can be termed "extract" or form the basis of an "extract" that is obtainable or obtained after subsequent processing such as, e.g., drying or the addition of excipients. Methods to extract plant material are well-known in the art and described for example in Gaedcke, Steinhoff, Herbal Medicinal Products, Medpharm Scientific Publishers, CRC Press 2003, ISBN: 0849310237. Extraction procedures may be based on a variety of parameters such as, e.g., weight, size or solubility/polarity, depending on the targeted compounds. Extraction in accordance with the invention is based on solubility. Solubility describes the capability of a substance to dissolve in a solvent and is a function of temperature, pressure and polarity.

A "solvent" in accordance with the invention is a substance that has the capability to dissolve the compounds that are contained in the plant material to be extracted to obtain the extract as comprised in the composition of the invention. In other terms, the solvent is capable to dissolve the desired plant compounds (also referred to herein as drug which form the extract) in the substrate plant material and form a solution containing the latter. Said solvent is, preferably, liquid, but may also be gaseous, such as $CO_2$, or solid, wherein in the latter case it can be liquefied to be used in an extraction process as described herein. Solvents can be classified according to their polarity from polar (hydrophil) to non-polar (lipophil). Generally, a polar solvent will dissolve polar compounds best, while non-polar solvents will dissolve non-polar compounds best. The dielectric constant of the solvent can be used for the classification of a solvent into a hydrophilic, medium-polar or lipophilic solvent, but also other means such as, e.g., the Grunwald Winstein mY scale or the Kosower's Z scale (Kosower, E. M., "An introduction to Physical Organic Chemistry", Wiley: New York, 1969, p. 293) can be used for classification. In accordance with the invention, a lipophilic solvent has a dielectric constant of <5, while a medium-polar solvent has a dielectric constant ranging from 5 to 20, and a hydrophilic solvent has a dielectric constant >20.

Hydrophilic solvents in accordance with the invention can be, e.g., polar branched or linear chain hydrocarbons, polar and medium polar organic compounds, chlorinated versions thereof, water or mixtures thereof. Preferably, said hydrocarbons have a C1 to C10 framework such as, e.g., C1 to C10 alcohols (e.g., n-butanol, isopropanol, n-propanol, ethanol or methanol) or acids (e.g., formic acid or acetic acid). Polar organic compounds are selected from the group consisting of acetone, dimethylformamide (DMF), acetonitrile (MeCN), dimethyl sulfoxide (DMSO) or propylene carbonate.

Medium-polar solvents in accordance with the invention can be, e.g., medium-polar organic compounds like, e.g., ethyl acetate, dichloromethane or tetrahydrofuran.

Lipophilic solvents in accordance with the invention can be, e.g., non-polar branched, aromatic or linear hydrocarbons or ethers (e.g., diethyl ether, 1,4-dioxane). Preferably, said hydrocarbons have a C1 to C10 framework such as, e.g., chloroform, toluene (also referred to as toluol), benzene, cyclohexane, hexane, cyclopentane or pentane.

Independent of the extraction method (see below), as a solvent for the extraction of a *Raphanus* plant preferably a lipophilic or medium-polar solvent, more preferred a lipophilic solvent is to be used, unless specified otherwise.

Also preferred is that the extraction is achieved by percolation, maceration, decoction or infusion using the solvents described herein.

The extraction procedure of percolation is well-known in the art and relates to the process of extracting plants by using a filter to separate drug, i.e. the desired plant compounds to be extracted, from plant parts when solvent is poured over plant parts and efflux containing the drug is captured. The extract yield is influenced by the solvent (concentration, polarity, and quantity), extraction time, extraction flow and extraction apparatus (volume of the batch, height). Extraction of *Raphanus* plants, preferably of the species *Raphanus sativus* or mixtures of *Raphanus* plants comprising plants of the species *Raphanus sativus*, by percolation is preferably performed using medium-polar solvent such as, e.g. ethanol/water mixtures. Extraction of *Therobroma* plants, preferably of the species *Theobroma cacao* or mixtures of *Theobroma* plants comprising plants of the species *Theobroma cacao*, by percolation is preferably performed using a hydrophilic solvent such as, e.g., a 20% acetone solution, water, methanol or a water/methanol mixture.

Maceration is an extraction procedure characterized by macerating the substrate plant material with the solvent for a given time period such as, e.g., 12 to 24 hours, or two or more days with optional (occasional) shaking and separating the liquid extract from the extracted plant material. In this procedure, the ratio of the herbal drug to the extraction solvent is a relevant factor for the effectiveness of extraction. The quantity of extractable matter is increased with the quantity (mass, volume) of extraction solvent because when using higher amounts of extraction solvent steady-state conditions are reached later. The ratio of the herbal drug to the extraction solvent is, therefore a relevant parameter for the quality of the extract and should be defined to ensure batch to batch conformity. Extraction of *Raphanus* plants, preferably of the species *Raphanus sativus* or mixtures of *Raphanus* plants comprising plants of the species *Raphanus sativus*, by maceration is preferably performed using a medium-polar solvent such as, e.g., ethanol/water mixtures. Extraction of *Therobroma* plants, preferably of the species *Theobroma cacao* or mixtures of *Theobroma* plants comprising plants of the species *Theobroma cacao*, by maceration is preferably performed using a relative hydrophilic solvent such as, e.g., a 20% acetone solution, pure water, methanol or a water/methanol mixture.

Decoction is an extraction procedure characterized by boiling the substrate plant material with solvent to the boiling temperature of the mixture. The extraction process generally takes a relatively long time compared to other extraction methods, in particular those described herein. After boiling the filtrate is separated from the used plant material. The quantity of extractable matter is increased with quantity (mass, volume). The temperature and extraction time are additional parameters which can have influence on the quantity of the native extract. Extraction of *Raphanus* plants, preferably of the species *Raphanus sativus* or mixtures of *Raphanus* plants comprising plants of the species *Raphanus sativus*, by decoction is preferably performed using a medium polar solvent such as, e.g., alcohol/water mixtures. Extraction of *Therobroma* plants, preferably of the species *Theobroma cacao* or mixtures of *Theobroma* plants comprising plants of the species *Theobroma cacao*, by decoction is preferably performed using a hydrophilic solvent such as, e.g., water or low concentration alcohol/water or acetone/water mixtures.

Infusion is an extraction procedure characterized by using a fixed quantity (mass/volume) of extraction solvent until the extractable matter is completely transferred from the herbal matrix to the solvent. The drug extract ratio may therefore vary from batch to batch within a certain range. It is influenced by the characteristics of the herbal drug (content of extractable matter, loss on drying, etc.). Herbal drug preparations manufactured by percolation procedures are described by average quantity (mass/volume) of extraction solvent with a defined range, e.g. 1:12 (1:10 to 1:14). The dimension is either mass/volume (m/v) of extraction solvent or mass/mass (m/m). The Extraction of *Raphanus* plants, preferably of the species *Raphanus sativus* or mixtures of *Raphanus* plants comprising plants of the species *Raphanus sativus*, by infusion is preferably performed using medium-polar solvents such as, e.g., alcohol/water mixtures. Extraction of *Therobroma* plants, preferably of the species *Theobroma cacao* or mixtures of *Theobroma* plants comprising plants of the species *Theobroma cacao*, by infusion is preferably performed using a hydrophilic solvent such as, e.g., water or low concentrated alcohol/water or low concentrated water/acetone mixtures.

The plant material used as substrate for the extraction process is, preferably, dry plant material, but can also be plant material that has not been processed or differently processed, because fresh plant material contains water which can promote the hydrolysis of natural compounds and can make a composition unstable. Further, and as known in the art, extraction efficiency is higher, if the plant substrate material is crushed, cut small or powderized, wherein the degree of the latter processing of the plant material depends on the chosen method to extract the plant substrate.

*Raphanus* is a genus within the plant family Brassicaceae. Currently, and in accordance with the invention, the genus comprises the species *Raphanus caudatus* (sometimes also regarded as a variety of *R. sativus*), *Raphanus raphanistrum* and *Raphanus sativus* including various artificial and natural varieties such as, e.g., *R. saphanistrum* ssp. *landram*, *R. raphanistrum* ssp. *maritimus*, "April Cross", "Bunny Tail" "Cherry Belle", "Champion", "Red King", "Sicily Giant", "Snow Belle", "White Icicle", "French Breakfast", "Plum Purple", "Black Spanish", "Black Spanish Round", or "Daikon" (*R. sativus* var. *longipinnatus*). In accordance with the invention, it is preferred that at least the air roots, seeds and/or bulbs are extracted. Preferably, only the latter plant parts are used as substrate plant material for extraction or, in case further *Raphanus* plant parts are used, as much as possible of the latter plant parts are used as substrate plant material for extraction. Preferably, in case further plants parts are used, the percentage of air roots, seeds and/or bulbs in the substrate plant material makes up or more than (for each value) 50%, 60%, 70%, 80%, more preferred 85% and 90%, and most preferred more than 95% of the substrate plant material used for extraction. As such, it also envisaged that additional plant parts can be extracted, even the whole plant. Preferably, the *Raphanus* plants used to obtain the substrate plant material are about 6 to 8 months old and/or are harvested between April and May.

*Theobroma* is a genus of plants in the Malvaceae (also called Sterculiaceae) family. Currently, and in accordance with the invention, the genus comprises the following species: *Theobroma angustifolium, Theobroma bicolor, Theobroma cacao, Theobroma canumanense, Theobroma grandiflorum, Theobroma mammosum, Theobroma microcarpum, Theobroma obovatum, Theobroma simiarium, Theobroma speciosum, Theobroma stipulatum, Theobroma subincanum, Theobroma sylvestre, Theobroma bernoulli, Theobroma gileri, Theobroma glaucum, Theobroma hylaeum, Theobroma sinuosum, Theobroma velutinum*. Also included in accordance with the invention are artificial and natural varieties. In accordance with the invention, it is preferred that at least the fruit is extracted. The fruit encompasses, e.g. the seeds. Preferably, only fruits are used as substrate plant material for extraction or, in case further *Theobroma* plant parts are used, as many fruits as possible are used as substrate plant material for extraction. Preferably, in case further plant parts are used, the percentage of fruits in the substrate plant material makes up or more than (for each value) 50%, 60%, 70%, 80%, more preferred 85% and 90%, and most preferred more than 95% of the substrate plant material used for extraction. As such, it also envisaged that additional plant parts can be extracted such as, e.g., the leaves, the bark, and again even the whole plant except the roots. Preferably, the *Theobroma* plants used to obtain the substrate plant material are about 10 to 20 years old, grown in a tropical rainforest region, such as West Africa or Central America, and/or are harvested between April and May.

It is also envisaged that the plant parts of two or more different species of the genera defined herein are used as substrate plant material for extraction. Preferably, and in the case of *Raphanus*, the species *Raphanus sativus* or mixtures of *Raphanus* plants comprising plants of the species *Raphanus sativus* are used as substrate plant material; in case of *Theobroma*, the species *Theobroma cacao* or mixtures of *Theobroma* plants comprising plants of the species *Theobroma cacao* are used as substrate plant material.

As mentioned above, the extract comprising solvent and dissolved plant compounds can generally, and also in accordance with the invention, be processed further, e.g., in order to purify and concentrate the extracted compounds. Concentration of the extracted compounds can be achieved, e.g., by minimizing the amount of solvent(s), e.g., by letting the solvent evaporate, by precipitation or other methods as described in, e.g., Gaedcke, Steinhoff, Herbal Medicinal Products, Medpharm Scientific Publishers, CRC Press 2003, ISBN: 0849310237. Purification can be achieved, e.g., by filtration methods, which are advantageously, but not necessarily, employed before the amount of solvent is minimized. Besides being a method for concentrating the extract, precipitation can also be used as a means to purify the extract, wherein the precipitate can be either the desired plant compound(s) or undesired impurities, both leading to a concentration and purification of the part of the extract comprising the desired compound(s). Preferably, the solution comprising the desired plant compound(s) and the solvents(s) is filtered and subsequently the filtrate is evaporated under vacuum to dryness. Selection of the parameters (choice of solvent, etc.) of the extraction process so that said filtration and said solvent evaporation is possible can be effected using standard procedures.

Thus, preferably and in generic terms, the extracts in accordance with the invention are obtainable or obtained by extracting the substrate plant material (which is preferably dried) with one or more solvents as defined herein followed by a subsequent filtration step before the filtered solution is dried to obtain the dried extract.

The dried extract can be further modified depending on the intended use, e.g., by adding excipients such as, e.g. maltodextrin and/or silica, for standardization purposes.

In the case of an extract of a plant belonging to the genus *Raphanus*, the extract is preferably standardized to contain 1% to 5% of total flavonoids such as 1.1% to 4.9%, 1.2% to 4.8%, 1.25% to 4.75%, 1.5% to 4.5%, 1.75% to 4.25%, more preferred 2% to 3% or 2.25% to 2.75% of total flavonoids. For example, said extract can be standardized to contain 1%, 1.25%, 1.5%, 3.25%, 3.5%, 3.75%, 4%, 4.5%, or more preferred 2%, 3% or most preferred 2.5% total flavonoids. In the case of an extract of a plant belonging to the genus *Theobroma*, the extract is preferably standardized to contain 3% to 20% of total procyanidins such as 4% to 19%, 5% to 18%, 6% to 17% or 16%, more preferred 6% to 14% or 15% and most preferred 7% to 12% or 13%, 8% to 10% or 11% of total procyanidins. For example, said extract can be standardized to contain 3%, 4%, 5%, 14%, 15%, 16%, 17%, 18%, more preferred 6%, 7%, 11% or 12%, and most preferred 8%, 9%, or 10% total procyanidins. The skilled person is in the position to standardize the extracts to the values referred to above by means known in the art and described herein, e.g., by adding excipients and/or adjusting the substrate plant material.

The combination of the extracts as defined herein was shown to be well tolerated in the in vivo studies with no side effects observed.

The present invention is based on the surprising finding that the mentioned combination of the extracts can be used as a pharmaceutical composition to combat opioid and alcohol abuse and symptoms of opioid and alcohol abuse. Specifically, the inventors performed a variety of tests with the compositions of the invention in animal models suitable to assess different effects of opioid and alcohol abuse. By assessing the behavior of rats in an intravenous self-administration model upon administration of the composition according to the invention, it could be demonstrated that morphine and heroin self-administration was significantly reduced (see Example 1). This evidences that the composition of the invention is capable of effectively reducing the reinforcing activity which indicates that said compositions are useful in combating abuse of opioids. Further, also performance of motor behavior was performed, which is a scientifically accepted model to analyze the effects of a given drug with respect to occurrence of hand tremors, memory performance, reaction time, hand eye coordination, accuracy, balance, visual search, response of skills, recognition, running, cycling times and overall performance (see Example 2). In human subjects the effectiveness to treat alcohol abuse was demonstrated as the symptoms associated with alcohol abuse could significantly diminished (see Example 4). Taken together, these results show that the composition of the invention is suitable to reduce the urge to administer alcohol or opioids and to minimize the symptoms accompanying withdrawal of alcohol and opioids. Neither plant alone has been described in this context before.

The knowledge about *Raphanus* and *Theobroma* plants and their potential significance in a medical scenario is summarized in the following. As regards constituents *Theobroma* plants are known to contain tannins and flavanoids like procyanidins in high concentration as well as other phenolic compounds like flavonoids. In *Theobroma cacao*, the flavonoid antioxidants have been shown to lower cholesterol levels by blocking cholesterol from gathering in blood vessels. Additionally, the antioxidants are considered to support the heart function. Studies show blood vessels are more relaxed by the antioxidants, effectively lowering blood pressure as well as increasing circulation (Ding et al., Nutr Metab (Lond), 3:2 (2006); (Khawaja et a., Curr Atheroscler Rep., 13:447-452 (2011)).

*Theobroma cacao* also contains arginine, an amino acid that helps build muscles as well as promote a faster recovery after working out. The benefits of arginine in this process allow for quicker recovery. Arginine is referred to as the 'aphrodisiac' ingredient, conferring a relaxed feeling and reducing stress. *Theobroma cacao* as well as other *Theobroma* species, comprises various further compounds that have an effect on mood such as, e.g., MAO inhibitors (monoamine oxidase enzyme inhibitors), anandamide, tyramine, serotonin, phenyl ethyl amine (PEA). These mood enhancers are thought to confer an energetic and happy feeling and motivation in personal improvements as exercise and weight loss. Xanthine derivatives like caffeine and theobromine are also found in *Theobroma cacao*. These provide energy that is sustained, rather than a temporary jolt which can leave a person jittery. Caffeine and theobromine further provide clarity and focus throughout the day. In addition, powerful appetite suppressants quiet the strong cravings that make dieting difficult. Chocolate is known to increase levels of neurotransmitters like phenyl ethylamine, serotonin, and anandamide in the brain. An imbalance in various neurotransmitters including serotonin has also been reported in subjects with CFS (chronic fatigue syndrome). The effect of cocoa in subjects with chronic fatigue syndrome has not been studied to date. It is hypothesized that chocolate, by modulating neurotransmitters, might reduce the symptom burden of CFS (di Tomaso et al., Nature, 382, 677-678 (1996)). The relationship between chocolate and mood are highly complex, combining psychopharmacological components, nutritional and sensory characteristics of the food. Individual and situational differences on chocolate consumption may also exert influence on mood and the mixed results in previous research indicate that the direction of the association remains unclear (Macht M. and Mueller J, J Nerv Ment Dis., 195(12):1024-6 (2007)). *Theobroma cacao* is also considered one of the best food sources of magnesium.

Cocoa intake was shown to be able to decrease specific IgG2a, IgG2b and IgG2c titres. Moreover, cocoa intake in CIA (collagen induced arthritis) rats reduced ROS (reactive oxygen species) production, TNFα and NO (nitric oxide) release from peritoneal macrophages, and decreased the Th:cytotoxic T cell ratio in ILN (inguinal lymph nodes). A cocoa flavonoid-enriched diet in LOU rats with CIA produced no effect on hind-paw swelling but was able to modulate the specific antibody response (Ramos-Romero S., et al., Br J Nutr, 107(3):378-87 (2012).

The inhibitory effect of PCE (polyphenol-enriched cocoa extract) on acute UC (ulcerative colitis) induced by DSS in mice was attenuated by oral administration of PCE obtained from cocoa. This effect is principally due to the inhibition of transcription factors STAT1 and STAT3 in intestinal cells, with NF-κB inhibition also being implicated (Andújar et al., Oxidative Medicine and Cellular Longevity, Vol. 2012: 1-23 (2012)). Also, cacao mass LCC (liquid column chromatography) has been shown to have anti-HIV activity (Sakagami H. et al., In Vivo, 25(2):229-36 (2011)).

It is known in the art that *Raphanus* plants' roots and leaves contain alkaloids, proteins, polysaccharides, flavonoids, glycosides, and phenolic compounds. A biological activity of cruciferous vegetables is hypothesized to be due to the metabolites of a class of phytochemicals called glucosinolates. The chemical properties of these metabolites, including isothiocyanates, determine the biological activity of these compounds and thus their effects on human health (Gutierrez R. M. and Perez R. L., Scientific World Journal, 4: 811-837 (2004)). HPLC identification of polyphenolics in the leaves of *R. sativus* indicated the presence of catechin, protocatechuic acid, syringic acid, vanillic acid, ferulic acid, sinapic acid, o-coumaric acid, myricetin, and quercetin in leaves and stem (Beevi et al., Plant Foods Hum Nutr., 65(1):8-17 (2010); Beevi et al., Nat Prod Res., 26(6): 557-63 (2012)).

Among the different extraction solvents, methanolic extract of leaves and stem showed potent reductive capacity, significantly inhibited linoleic acid peroxidation and displayed metal chelating activity. Further, they scavenged free radicals effectively with $IC_{50}$ (half maximal inhibitory concentration) of 31 and 42 µg/ml for DPPH radical, 23 and 52 µg/ml for superoxide radical, 67 and 197 µg/ml for hydrogen peroxide, and 56 and 62 µg/ml for nitric oxide, respectively. Leaves showed most potent antioxidant and radical scavenging activity as compared to stem, which may be accounted for the high polyphenolic content. Leaves and stem of *R. sativus*, an often under-utilized part of this vegetable, thus possessed considerable amount of polyphenolics.

The efficacy of different parts of *R. sativus* such as root, stem and leaves, extracted with solvents of varying polarity were tested (Beevi et al., Plant Foods Hum Nutr., 65(3): 200-9 (2010)). The molecular mechanism leading to growth arrest and apoptotic cell death in human cancer cell lines was investigated. *R sativus* showed chemopreventive significant growth inhibitory effect with the hexane extract. Raphasatin isolated from *R. sativus*, but not its degradation products, activated the antioxidant response element (ARE) in a stably-transfected reporter cell line. Mice fed a diet consisting of 20% freeze dried radishes for 2 weeks had significantly higher liver expression of cytochrome P450 (CYP) 1A1, 1A2, quinone reductase, microsomal epoxide hydrolase, and glutathione S-transferase α2 than mice fed a nutritionally-matched control diet (Scholl et al., J Food Sci., 76(3):C504-11 (2011)).

The aqueous extract of the bark of *R. sativus* was tested for its anti urolithiatic and diuretic activity (Vargas et al., Journal of Ethnopharmacology 68, pp. 335-338 (1999)). Significant decrease in the weight of stones was observed after treatment in animals which received aqueous extract in comparison with control groups. This extract showed an increase in the 24 h urine volume as compared to the control.

The antidiabetic effect of *R. sativus* was additionally studied and it could be shown that blood glucose levels could be lowered (Shukla et al, Pharm Biol., 49(1):32-7 (2011)).

A surprising finding is the capacity of *Raphanus* extracts to modulate the brain's dopamine concentration. It is postulated in the scientific world that the rewarding effects of many drugs of abuse are, to some extent, all mediated by the mesolimbic dopaminergic pathway originating in the ventral tegmental area and innervating the nucleus accumbens. Although through different mechanisms, opioids, stimulants, ethanol and nicotine all increase extracellular levels of dopamine in the nucleus accumbens. Without being limited to a specific scientific theory as to the action of the compositions of the invention, it could, on the one hand, be shown that—consistent with the demonstrated anti-addictive effects of said compositions of the invention—the dopamine release in the nucleus accumbens could be decreased (even within the first 2 hours of administration; data not shown). On the other hand, as evident from Example 5, below, it could also be demonstrated that the extract of *Raphanus* resulted in an increase of dopamine within 30 minutes after administration. Also an increase in dopamine levels is beneficial in the treatment of drug addicts as defined herein below, e.g., in treating the aspect of depression associated with opioid/alcohol addiction and/or opioid/alcohol withdrawal. Thus, modulation of the brain's dopamine concentration is beneficial in the treatment of drug addiction and in treating the symptoms of withdrawal as defined herein below.

As outlined herein above, currently potential treatments for drug abuse are targeted at a specific drugs or drug classes of abuse. The compositions of the invention, however, are effective in treating multiple forms of drug abuse, i.e. opioid and alcohol abuse, as well as in treating the symptoms of opioid and alcohol withdrawal. Furthermore, the compositions of the invention are believed to act on several receptors, such as the opioid receptors, altogether showing a synergistic effect. They also reduce essentially all or at least the main symptoms of opioid and/or alcohol withdrawal and have a sedative and anti-depressant activity while side effects were low.

In a preferred embodiment of the composition of the invention, said solvent of a) is selected from the group consisting of water, an alcohol, a water/alcohol mixture, a ketone, a water/ketone mixture, $CO_2$, ethyl actetate, hexane and chlorinated forms thereof; and/or wherein said solvent of b) is selected from the group consisting of water, an alcohol, a water/alcohol mixture, a ketone and a water/ketone mixture.

Alcohols that can be used according to this preferred embodiment are, preferably, selected from the group consisting of methanol, ethanol, butanol, propanol, isopranopnol, propylene glycol, glycerol and combinations thereof. Preferably, methanol or ethanol is used as a solvent either alone or in a combination of, e.g., 30% methanol and 70% ethanol. Alcohols, in particular the aforementioned group of alcohols, can each also be used in admixture with water as a solvent, i.e. the solvent is a water/alcohol mixture. Preferably, the percentage of alcohol in a corresponding mixture is 25% to 95% such as, e.g., 30% to 90%, 40% to 80%, 50% to 70%, 30%, 50% or 70%, while also higher and lower alcohol percentages such as 10%, 15%, 20%, 80% or 90% are envisaged. Preferably, an ethanol/water mixture with 30% to 90%, 40% to 80%, 50% to 70%, 30%, 50% or 70% ethanol, or a methanol/water mixture with 30% to 90%, 40% to 80%, 50% to 70%, 30%, 50% or 70% methanol is used as solvent.

Ketones that can be used in accordance with the invention are, preferably, selected from the group consisting of acetone and butanone (also known as methyl ethyl ketone). Preferably, acetone is used as a solvent. Ketones, in particular the aforementioned group of ketones, can each also be used in admixture with water as a solvent, i.e. the solvent is a water/ketone mixture. Preferably, the percentage of ketone in a corresponding mixture is 25% to 95% such as, e.g., 30% to 90%, 40% to 80%, 50% to 70%, 30%, 50% or 70%, while also higher and lower ketone percentages such as 10%, 15%, 20%, 80% or 90% are envisaged. For example, *Theobroma* plants can be extracted by a ketone/water mixture of 10% or 20% ketone. Preferably, an acetone/water mixture with 30% to 90%, 40% to 80%, 50% to 70%, 30%, 50% or 70% acetone is employed.

Ethyl acetate is in accordance with the definition given herein above a medium-polar solvent (also referred to in the art as polar aprotic solvent). Preferably, ethyl acetate is used at a temperature of between 40 to 60° Celsius, more preferred in combination with low pressure.

Hexane is in accordance with the definition given herein above a non-polar solvent. Preferably, hexane is used at a temperature of between 40 to 60° Celsius, more preferred in combination with low pressure.

$CO_2$ is in accordance with the definition given herein above a non-polar solvent and in a fluid state where it is held at or above its critical temperature and critical pressure, also known in the art as supercritical $CO_2$ (also referred to as $scCO_2$). Standard conditions of temperature and pressure for $CO_2$ extractions are temperatures of 30 to 50° C. at a pressure of 300 to 400 bar and very small amounts of liquid solvents (see, e.g., He et al., Int J Mol Sci., 13(10):13065-78 (2012)).

In a further preferred embodiment of the composition of the invention, said extract of a) with a drug-extract ratio of 4-7.5:1 and said extract of b) with a drug-extract ratio of 3-8:1 are present in the composition at a ratio of about 1.5 to about 6.5 parts of said extract of a) and about 3.5 to about 7.5 parts of said extract of b).

The "drug-extract ratio" (also abbreviated as DER) is a parameter well-known in the art and refers to the ratio between the quantity of substrate plant material (comprising the desired plant compounds to be extracted) used in the manufacture of the plant extract and the quantity of dried plant extract obtained, wherein the dried plant extract is not admixed with further substances such as, e.g., excipients etc., but relates to the extract of endogenous plant compounds (see, e.g., "Fundamentals of Pharmacognosy and Phytotherapy" by Michael Heinrich, Joanne Barnes, Simon Gibbons, Elizabeth M. Williamson), Elsevier Science, First edition, 2004, ISBN:-10: 0443071322, Chapter 9, P. 144-159). The number written before the colon is the relative quantity of the substrate plant material, whereas the number written after the colon is the relative quantity of the dried plant extract obtained. The person skilled in the art is in the position to adjust the various parameters of an extraction process such as, e.g., solvent, temperature, extraction method, to achieve the drug-extract rations as specified herein for each plant extract using his/her common general knowledge or standard experiments (see, e.g., also "Fundamentals of Pharmacognosy and Phytotherapy" as mentioned above). For example, a *Raphanus* extract, e.g., a *Raphanus sativus* extract, with a drug-extract ratio of 4-7.5:1 can be obtained or is obtainable by using medium-polar and/or lipophilic solvent (such as 50% water/ethanol mixture), and/or by using as extraction method maceration. Without limitation, a *Theobroma* extract, e.g., a *Theobroma cacao* extract, with a drug-extract ratio of 3-8:1 can be obtained or is obtainable by using a hydrophilic and/or medium-polar solvent (such as, e.g. a 10% or 20% ethanol/water mixture or 10% or 20% acetone/water mixture or a 40 to 60% ethanol/water or 40 to 60% acetone/water mixture), and/or by using as extraction method maceration, optionally using a temperature of below 40° Celsius, e.g., in the case of ethanol as solvent.

The term "about" as used herein with regard to numeric values, in particular in the context of the ratios of the various extracts to each other as comprised in the compositions of the invention, is meant to refer to an average deviation of maximum +/−10%, preferably +/−5% such as +/−2.5%, +/−1.25% or +/−0.625%. At the same time, the specification also refers to said numeric values, e.g., the mentioned ratio values, without the term "about", i.e. the specification also refers to said ratio values per se without taking into account an average deviation.

In the context of the relative amount of extracts a) and b) to each other, i.e. the ratio at which they are present in the composition, the term "parts" means either mass/mass (abbreviated as m/m) or volume/volume (abbreviated V/V).

More preferred extract a) to extract b) ratios (written in the format a):b)) are selected from the group consisting of 2-6:4-7 (i.e. 2-6 parts of extract a):4-7 parts of extract b)), 3-5:4-6. Even more preferred is a ratio of 4-5:1.

In another preferred embodiment of the composition of the invention, the composition further comprises c) an extract of a plant belonging to the genus *Passiflora*, wherein said extract is obtainable or obtained by extracting at least the flower with a hydrophilic, medium-polar and/or lipophilic solvent; and/or d) an extract of a plant belonging to the genus *Crocus*, wherein said extract is obtainable or obtained by extracting at least the flower with a hydrophilic, medium-polar and/or lipophilic solvent.

*Passiflora* is a genus in the family of Passifloraceae. Said genus comprises more than 500 species. Also included in accordance with the invention are artificial (horticultural hybrids) and natural varieties. In accordance with the invention, it is preferred that at least the flower is extracted. Preferably, only the latter plant part is used as substrate plant material for extraction or, in case further plant parts are to be used, as much as possible of the latter plant part is used as substrate plant material for extraction. Preferably, in case further plants parts are used, the percentage of flowers in the substrate plant material makes up or more than (for each value) 50%, 60%, 70%, 80%, more preferred 85% and 90%, and most preferred more than 95% of the substrate plant material used for extraction. As such, it is also envisaged that additional plant parts can be extracted, even the whole plant. Preferably, the plant parts, in particular the flowers, are to be harvested from, preferably, at least three year old specimens in the spring after the *Passiflora* plants form buds. Also preferred is that *Passiflora* plants cultivated in Brazil, preferably on a soil that drains well, are harvested.

In the following, a summary of the current knowledge about the constituents and properties of plants of the genus *Passiflora* is provided. Many species have been found to contain beta-carboline harmala alkaloids, which are MAO inhibitors with anti-depressant properties. The flower and fruit have only traces of these chemicals, but the leaves and the roots are often more potent and have been used to potentiate the effects of mind-altering drugs. The most common of these alkaloids is harman (1-methyl-9H-b-carboline), but harmaline (4,9-Dihydro-7-methoxy-1-methyl-3H-pyrido[3,4-b]indole), harmalol (1-methyl-2,3,4,9-tetrahydropyrido[3,4-b]indol-7-one), harmine (7-Methoxy-1-methyl-9H-pyrido[3,4-b]indole) and harmol have also been identified. Many flavonoids and their glycosides have been found in *Passiflora*, including apigenin, benzoflavone homoorientin, 7-isoorientin, isoshaftoside, isovitexin (or saponaretin), kaempferol, lucenin, luteolin, n-orientin, passiflorine (named after the genus), quercetin, rutin, saponarin, shaftoside, vicenin and vitexin. Maypop, Blue Passion Flower (*P. caerulea*), and perhaps others contain chrysin, a flavone with confirmed anxiolytic and anti-inflammatory, supposed aromatase inhibitor properties. Also documented to occur at least in some *Passiflora* species in quantity are the hydrocarbon nonacosane and the anthocyanidin pelargonidin-3-diglycoside. As regards organic acids, the genus is rich in formic, butyric, linoleic, linolenic, malic, myristic, oleic and palmitic acids as well as phenolic compounds, and the amino acid α-alanine. Esters like ethyl butyrate, ethyl caproate, n-hexyl butyrate and n-hexyl caproate give the fruits their flavor and appetizing smell. Sugars, contained mainly in the fruit, are most significantly D-fructose, D-glucose and raffinose. Among enzymes, *Passiflora* species were found to be rich in catalase, pectin methylesterase and phenolase.

The various constituents of *Passiflora* plants have been shown to have various therapeutically useful effects as laid out in the following. The fresh or dried flowers of various *Passiflora* species are used to make a tea that is used to treat insomnia, hysteria, and epilepsy, and is also valued for its analgesic properties. *P. edulis* (passion fruit) and a few other species are used in Central and South America for similar purposes. Once dried, the leaves can also be smoked. The medical utility of very few species of *Passiflora* has been scientifically studied. In initial trials for treatment of generalized anxiety disorder, maypop extract performed as well as oxazepam, but with fewer short-term side effects. It was recommended to follow up with long-term studies (Akhondzadeh et al., Journal of Clinical Pharmacy and Therapeutics, vol. 26, issue 5, p. 363-367, (2001)). *Passiflora incarnate* is listed in the pharmacopoeias of Great Britain, United States, India, France, Germany, Switzerland and others (Dhawan et al., J Ethnopharmacol.; 78(2-3):165-70 (2001)). The active ingredients responsible for a potential pharamceutical effect have not been conclusively defined (Carlini E A, Plants and the central nervous system. Pharmacology, Biochemistry and Behavior. 2003; 75:501-512). Most available data suggests flavonoids as possible active ingredients (Speroni and Minghetti, Planta Med.; 54(6):488-91 (1988); Dhawan et al., J Ethnopharmacol.; 78(2-3):165-70 (2001); Dhawan et al., J Pharm Pharmaceut Sci., 6(2): 215-222 (2003)).

Studies in animal models show efficacy of *Passiflora* extracts and flavonoid fractions against pentylenetetrazol (PTZ) induced seizures (Speroni and Minghetti, Planta Med., 54(6):488-91 (1988); Speroni and Billi, Phytotherapy Research, 10:S92-S94 (1996); Nassiri-Asl et al., BMC Complement Altern Med., 8; 7:26 (2007); Nassiri-Asl et al., Progess in Neuro-Psychopharmacology and Biological Psychiatry, 32:989-993 (2008)). In 3 clinical trials, *Passiflora* extracts showed anxiolytic efficacy. One of the trials compared *Passiflora* to placebo (Movafegh et al., Anesth Analg., 106(6):1728-32 (2008)), and two others showed *Passiflora* to have anxiolytic efficacy similar to benzodiazepines (Mori et al., Rinsho Hyoka [Clinical evaluation for drugs], 21(3): 383-440 (1993); Akhondzadeh et al., J Clin Pharm Ther., 26(5):363-7 (2001)). In addition, *Passiflora* extract showed sedative effects in 2 clinical trials (Akhondzadeh et al., J Clin Pharm Ther., 26(5):369-73 (2001); Movafegh et al., Anesth Analg., 106(6):1728-32 (2008)). The results of a study (Singh et al., Journal of Ethnopharmacology, Volume 139, issue 1, p. 273-279 (2012)) concluded that the hydroethanolic extract of *Passiflora incarnate* suppresses PTZ-induced seizures, and ameliorates its associated post-ictal depression, which has been found to be get worsened with the standard antiepileptic drug, diazepam. Oral preoperative administration of *Passiflora incarnata* suppresses the increase in anxiety before spinal anesthesia without changing psychomotor function test results, sedation level, or hemodynamics. The active alkaloids in passionflower—harmine and harman—affect levels of GABA, the neurotransmitter targeted by benzodiazepine medications like Valium and Xanax. Recently, the value of passionflower in treating opiate withdrawal has become apparent. According to National Institutes of Health, the use of passionflower along with Clonidine during opiate withdrawal results in better symptom relief than by the use of Clonidine alone. Further studies are needed, but, in accordance with the present invention, it is considered that inter alia the relaxing properties of passionflower can be useful in easing the symptoms of opioid and alcohol withdrawal.

*Crocus* is a genus in the family Iridaceae, subfamily Crocoideae. Various species exist and are well-known to the skilled person. These species can be classified according to Mathew (Brian Mathew, *Crocus*: A Revision of the Genus *Crocus*, Timber Press, 1983. ISBN 0-917304-23-3) in i) section *Crocus* comprising the series *Verni, Baytopi, Scardici, Versicolores, Longiflori, Kotschyani, Crocus*; and in ii) section *Nudiscapus* comprising the series *Reticulati, Biflori, Speciosi, Orientales, Flavi, Aleppici, Carpetani, Intertexti* and *Laevigatae*. In accordance with the invention, it is preferred that at least the flower is extracted. Preferably, only the latter plant part is used as substrate plant material for extraction or, in case further plant parts are to be used, as much as possible of the latter plant part is used as substrate plant material for extraction. Preferably, in case further plants parts are used, the percentage of flowers in the substrate plant material makes up or more than (for each value) 50%, 60%, 70%, 80%, more preferred 85% and 90%, and most preferred more than 95% of the substrate plant material used for extraction. As such, it also envisaged that additional plant parts can be extracted, even the whole plant. The plant parts, in particular the flowers, are preferably harvested from plants cultivated in Greece, Spain and Iran and in countries where annual rainfall averages 400-1000 mm. Generous spring rains and drier summers are optimal. Planting is preferably done in June, Harvests are by necessity a speedy affair: after blossoming at dawn, flowers quickly wilt as the day passes. All plants bloom within a window of one or two weeks.

In the following, a summary of the current knowledge about the constituents and properties of plants of the genus *Crocus* is provided: In view of its wide range of medical uses known today, the well-known spice saffron (see e.g., Negbi, M. (editor), *Saffron: Crocus sativus L.*, CRC Press (1999), ISBN: 987-90-5702-394-1) derived from *Crocus sativus* has undergone extensive phytochemical and biochemical studies and variety of biologically active ingredients has been isolated. Saffron contains more than 150 volatile and aroma-yielding compounds. Characteristic components of saffron are crocin (responsible for the color), picrocrocin (responsible for the bitter taste), and safranal (responsible for odor and aroma). It also has many non-volatile active components, many of which are carotenoids including zeaxanthin, lycopene, and various α- and β-carotenes. The volatiles with a very strong odor are consistent of more than 34 components that are mainly terpenes, terpene alcohols, and their esters. Non-volatiles include 14 crocins that are responsible for the red or reddish brown color of stigmas together with carotenes, crocetin, picrocrocin (a glycosidic precursor of safranal), the bitter substance and safranal the major organoleptic principle of stigmas. However saffron's golden yellow-orange color is primarily due to α-crocin. This crocin is trans-crocetin di-(β-d-gentiobiosyl) ester. Systematic (IUPAC) name: 8, 8-diapo-8, 8-arotenoic acid. This means that the crocin underlying saffron's aroma is a digentiobiose ester of the carotenoid crocetin. Crocins themselves are a series of hydrophilic carotenoids that are either monoglycosyl or diglycosyl polyene esters of crocetin. Crocetin is a conjugated polyene dicarboxylic acid that is hydrophobic and thus oil soluble. When crocetin is esterified with two water-soluble gentiobioses (which are sugars), a product results that is itself water soluble. The resultant α-crocin is a carotenoid pigment that may comprise more than 10% of dry saffron's mass.

*C. sativus* has been shown in the art to have anti-depressant effects, two active anti-depressant ingredients are crocin and safranal. As preliminary phytochemical results indicated, it could be suggested that the antinociceptive and anti-inflammatory effects of the petal extracts may be caused by their content of flavonoids, tannins, and anthocyanins. Other studies have demonstrated that various flavonoids such as rutin, quercetin, luteolin, hesperidin, and bioflavonoids are present (Srivastava et al., Pharmacogn Rev., 4(8):200-8 (2010)).

Fatehi and others (J Ethnopharmacology, 84:199-203 (2003)) investigated the effects of *C. sativus* petals' extract on blood pressure in anesthetized rats and also on responses of the isolated rat vas deferens and guinea pig ileum induced by electrical field stimulation (EFS). Aqueous and ethanol extracts of *C. sativus* petals' reduced the blood pressure in a dose-dependent manner.

In one of the studies, the anticonvulsant activities of *C. sativus* stigma constituents, safranal and crocin, were evaluated in mice using pentylenetetrazole (PTZ)-induced convulsions in mice. Safranal (0.15 and 0.35 ml/kg body weight, i.p.) reduced the seizure duration, delayed the onset of tonic convulsions, and protected mice from death. Crocin (22 mg/kg, i.p.) did not show anticonvulsant activity.

The ethanolic extract of *C. sativus* and safranal has been shown to reduce the number of cough (Hosseinzadeh et al., Fitoterapia, 77:446-8 (2006)).

Another study indicates that treatment with crocins of *C. sativus* L. induces anxiolytic-like effects in the rat (Pitsikas et al., Phytomedicine, 15:1135-9 (2008)).

To study the mechanism(s) of the relaxant effects of *C. sativus*, the stimulatory effect of aqueous-ethanolic extracts of this plant and one of its constituents, safranal, was examined on β-adrenoreceptors in tracheal chains of guinea pigs. The results indicated a relatively potent stimulatory effect of the extract from *C. sativus* on $\beta_2$-adrenoreceptors, which is partially due to its constituent, safranal. A possible inhibitory effect of the plant on histamine ($H_1$) receptors was also suggested in the art (Nemati et al., Phytomedicine, 15:1038-45 (2008)).

The efficacy of petal of *C. sativus* was assessed in the treatment of mild-to-moderate depression in a 6-week double-blind, placebo-controlled and randomized trial. The results of this study indicate the efficacy of petal of *C. sativus* in the treatment of mild-to-moderate depression. In further preliminary work, saffron was compared to the drug fluoxetine; it was found that the saffron performed as well as the drug in the treatment of depression (Moshiri et al., Phytomedicine, 13:607-11 (2006)).

In another study, the saffron extract and two of its main ingredients, crocin and crocetin, improved memory and learning skills in ethanol-induced learning behavior impairments in mice and rats. Oral administration of saffron is hypothesized in the art to be useful in the treatment of neurodegenerative disorders and related memory impairment. Thus, using these substances was postulated in the art to be useful in pharmacological alleviation of cognitive deficits (Sigiura et al., Phytother Res., 9:100-4 (1995)).

A further study showed that crocin analogs isolated from saffron significantly increased the blood flow in the retina and choroid as well as facilitated retinal function recovery and it could be used to treat ischemic retinopathy and/or age-related macular degeneration (Xuan B., J Ocul Pharmacol Ther, 15:143-52 (1999)).

Another study (Ghoshooni et al., Pak J Biol Sci., 14(20): 939-44 (2011)) was on the saffron ethanolic extract and its constituent, safranal. This study was an investigation on the acquisition and expression of morphine-induced place preference (CPP) in male Swiss Webster mice (20-25 g). An unbiased place conditioning method was applied for assessment of morphine reward properties. The saffron extract and safranal were administered intraperitoneally (i.p.) during (acquisition) or after induction (expression) of morphine CPP. In a pilot study, the extract and safranal were alone administered to the animals to assess if they have any reward properties. Subcutaneous (s.c.) of morphine (4 and 8 mg kg(−1)) and extract (50 mg kg(−1); i.p.) induced CPP. Extract (10, 50 and 100 mg kg(−1); i.p.) reduced the acquisition and expression of morphine CPP. The same results were obtained when safranal (1, 5 and 10 mg kg(−1), i.p.) was used. It may be concluded that both ethanolic saffron extract and safranal can inhibit the acquisition and expression of morphine-induced CPP in the mice.

As evident from the above, and without being bound to a specific theory, it is considered that in particular the antidepressant, relaxing and potential effects associated with CPP of *Crocus* plants are beneficial when used as part of the composition in accordance with the invention comprising an extract of *Raphanus* and *Theobroma* and, optionally, *Passiflora*.

The definitions, combinations and specific examples of solvents described herein above also apply mutatis mutandis to this preferred embodiment with regard to *Passiflora* and *Crocus* extraction unless specified otherwise. Therefore, said solvent of c) and d) is, preferably, selected from the group consisting of water, an alcohol, a water/alcohol mixture, a ketone, a water/ketone mixture, $CO_2$, ethyl acetate, hexane and chlorinated forms thereof. More preferred is the use of ethanol as solvent for the *Passiflora* extraction and any aqueous solvent described herein above such as a water/ethanol mixture for the *Crocus* extraction. Also preferred is that extraction is performed by percolation or maceration.

In the case of an extract of a plant belonging to the genus *Passiflora*, the extract is preferably standardized to contain 1% to 5% of total flavonoids using vitexin as readout such as 1.1% to 4.9%, 1.2% to 4.8%, 1.25% to 4.75%, 1.5% to 4.5%, 1.75% to 4.25%, more preferred 1.5% to 3% or 1.5% to 2.5% of total flavonoids. For example, said extract can be standardized to contain 1%, 1.25%, 1.5%, 3.25%, 3.5%, 3.75%, 4%, 4.5%, or more preferred 1.75%, 2.5% or most preferred 2% total flavonoids.

In the case of an extract of a plant belonging to the genus *Crocus*, the extract is preferably standardized to contain 1% to 5% of safranal such as 1.1% to 4.9%, 1.2% to 4.8%, 1.25% to 4.75%, 1.5% to 4.5%, 1.75% to 4.25%, more preferred 1.5% to 3% or 1.5% to 2.5% of safranal. For example, said extract can be standardized to contain 1%, 1.25%, 1.5%, 3.25%, 3.5%, 3.75%, 4%, 4.5%, or more preferred 1.75%, 2.5% or most preferred 2% of safranal.

In a more preferred embodiment of the composition of the invention, said extract of a) with a drug-extract ratio of 4-7.5:1, said extract of b) with a drug-extract ratio of 3-8:1 and said extract of c) with a drug-extract ratio of 5-7:1 are present in the composition at a ratio of about 0.5 to about 5 parts of said extract of a), about 2.75 to about 4 parts of said extract of b) and about 2.5 to about 5.5 parts of said extract of c).

In a further more preferred embodiment of the composition of the invention, said extract of a) with a drug-extract ratio of 4-7.5:1, said extract of b) with a drug-extract ratio of 3-8:1 and said extract of d) with a drug-extract ratio of 0.5-5:1 are present in the composition at a ratio of about 1 to about 4 parts of said extract of a), about 3 to about 4 parts of said extract of b) and about 1 to about 3.5 parts of said extract of d).

In an additional more preferred embodiment of the composition of the invention, said extract of a) with a drug-extract ratio of 4-7.5:1, said extract of b) with a drug-extract ratio of 3-8:1, said extract of c) with a drug-extract ratio of 5-7:1 and said extract of d) with a drug-extract ratio of 0.5-5:1 are present in the composition at a ratio of about 0.5 to about 4 parts of said extract of a), about 2.5 to about 3 parts of said extract of b), about 2.5 to about 5.25 parts of said extract of c) and about 0.5 to about 3.75 parts of said extract of d).

In an even more preferred embodiment of the composition of the invention, the said extract of a), said extract of b), said extract of c) and said extract of d) are present in the composition at a ratio of about 2.5 parts of said extract of a), about 3 parts of said extract of b), about 2.5 parts of said extract of c) and about 1.5 parts of said extract of d).

As evident from the example section, a corresponding composition showed a particularly good effectivity.

In a further preferred embodiment of the composition of the invention, the composition further comprises olive oil.

The addition of olive oil to the composition is preferred, because it is good carrier and it promotes the solubility of the extracts. Olive oil is a fat obtained from the olive and various methods for its production are well-known in the art since centuries (see, e.g., Olive oil production on bronze age Crete: nutritional properties, processing methods and storage life of Minoan olive oil. Riley, F. R.: Oxford Journal of Archaeology, Volume 21, Issue 1, pages 63-75, February 2002). In accordance with the invention, virgin olive oil is preferred over pomace oil, i.e. chemically extracted olive oil. Also preferred is cold extracted olive oil, i.e. extracted, preferably, at temperatures not exceeding 27° C. Preferably, the olive variety used for olive oil generation is *Olea europea* which is preferably harvested in a Mediterranean country.

The ratio of added olive oil to the entirety of extracts a), b), or a), b) and c), and/or d) in the composition resulting from the addition of olive oil is, preferably, 1 part olive oil to 4 parts extracts in mass.

In another preferred embodiment of the invention, the composition of the invention is a pharmaceutical composition.

The term "pharmaceutical composition", as used herein, relates to a composition for administration to a patient, preferably a human patient. As such, the pharmaceutical composition of the invention either consists of the plant extracts, and optionally olive oil, as defined herein above or it comprises further agents such as, e.g., a pharmaceutically acceptable carrier, excipient, diluent and/or a further pharmaceutically active agent. Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose, e.g., the doses outlined herein below.

The composition may be in solid or, preferably, in liquid form and may be, inter alia, in a form of (a) powder(s), (a) tablet(s), (a) capsule(s) or (a) solution(s). Due to the ease of manufacture, and administration, a more preferred dosage form is a soft gel capsule comprising the compositions of the invention, preferably the composition of the invention comprising olive oil.

Administration of the suitable compositions may be effected by different ways, preferably by non-parenteral methods such as, preferably, by oral administration. The dosage regimen can be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. The composition may be administered in a dosage between 1 mg and 100 mg/kg body weight per day also depending on the chosen potency of the plant extracts within the composition of the invention; however, doses below or above this exemplary range are envisioned, especially considering the aforementioned factors and chosen dilution of the pharmaceutically active matter, i.e. the plant extracts of the compositions of the invention. Progress can be monitored by periodic assessment.

Preparations for oral administration include, e.g., (sterile) aqueous or non-aqueous solutions, suspensions, and emulsions. Examples of non-aqueous solvents are propylene glycol, polyethylene glycol, vegetable oils, and organic esters such as ethyl oleate. Aqueous carriers include water, alcoholic/aqueous solutions, emulsions or suspensions, including saline and buffered media. Vehicles include sodium chloride solution, Ringers dextrose, dextrose and sodium chloride, lactated Ringers, or fixed oils. Such vehicles include fluid and nutrient replenishers, electrolyte replenishers (such as those based on Ringers dextrose), and the like. Preservatives and other additives may also be present such as, for example, antimicrobials, anti-oxidants, chelating agents, and inert gases and the like. It is also envisaged that said pharmaceutical composition comprises further pharmaceutically active agents known in the art to be effective in the treatment of the conditions mentioned herein, e.g., treating conditions or diseases associated therewith. Conventional excipients include binding agents, fillers, lubricants and wetting agents. Preferably, the compositions of the invention are administered orally taking the form of a soft gelatin capsule suitable for dissolving in the intestine (and releasing the compositions of the invention). It is known in the art that this form of administration allows a fast absorption of ingested compounds. In this case it is preferred that the composition with added olive oil described herein above is utilized with or without further agents as defined herein. However, the addition of another plant oil or additional plant oil such as, e.g., linen seed oil or black cumin seed oil is also envisaged.

In another embodiment of the invention, the pharmaceutical composition of the invention is for use in treating opioid abuse, opioid dependency, alcohol abuse and/or alcohol dependency and/or for use in treating the symptoms of opioid and/or alcohol withdrawal.

Alcohol abuse and alcohol dependency are conditions well-known in the art to describe the recurring use of alcoholic beverages despite negative consequences. Various classification systems exist according to which a person can be diagnosed to suffer from alcohol dependency and alcohol abuse. In accordance with the invention, all said classification systems can be used for diagnosis of a patient to be eligible for treatment as described herein. Specifically, classification according to the Diagnostic and Statistical Manual of Mental Disorders (DSM) can be used or the World Health Organization. According to the current edition (DSM-IV) the criteria for alcohol dependence include tolerance; withdrawal symptoms or clinically defined Alcohol Withdrawal Syndrome; use in larger amounts or for longer periods than intended; persistent desire or unsuccessful efforts to cut down on alcohol use; time is spent obtaining alcohol or recovering from effects of alcohol consumption; social, occupational and recreational pursuits are given up or reduced because of alcohol use; and use is continued despite knowledge of alcohol-related harm (physical or physiological). At least three criteria must manifest in a period of 12 months. For example, the so-called Alcohol Use Disorders Identification Test (AUDIT; see Babor et al., AUDIT, The Alcohol Use Disorders Identification Test, Guidelines for Use in Primary Care, Second Edition, World Health Organization, Department of Mental Health and Substance Dependence) can be used as a screening tool for identifying potential alcohol misuse ( ). A test more specifically directed at diagnosing alcohol dependency is the Severity of Alcohol Dependence Questionnaire (SAD-Q). Alcohol dependence is differentiated from alcohol abuse by the presence of symptoms such as tolerance and withdrawal. Alcohol abuse can lead to alcohol dependence. Currently, and for the next issue of DSM (DSM-V) it is envisioned that alcohol abuse and alcohol dependence are combined into one unified disorder, i.e. alcohol use disorder (AUD), which would include graded clinical severity from moderate to severe accounting for the differences between alcohol abuse and dependency. In accordance with said classification, the invention also relates to the treatment of a disease including the diseases alcohol abuse and alcohol dependence as laid out above.

Opioid abuse and opioid dependency are conditions equally well-known in the art. Again, in DSM-IV criteria for substance dependence and substance abuse have been defined. Once a thorough patient assessment has been performed, a formal diagnosis of either opioid dependence or abuse should be made. A substance dependence or abuse diagnosis, according to current DSM-IV diagnostic scheme, is based on clusters of behaviors and physiological effects occurring within a specific time frame. The diagnosis of dependence always takes precedence over that of abuse, e.g., a diagnosis of abuse is made only if DSM-IV criteria for dependence have never been met.

Dependence is defined as the occurrence of at least three of the following criteria within a period of 12 months: Tolerance (marked increase in amount; marked decrease in effect); characteristic withdrawal symptoms; substance taken to relieve withdrawal; substance taken in larger amount and for longer period than intended; persistent desire or repeated unsuccessful attempt to quit; much time/activity to obtain, use, recover; important social, occupational, or recreational activities given up or reduced; and use continues despite knowledge of adverse consequences (e.g., failure to fulfill role obligation, use when physically hazardous).

Abuse is defined as the occurrence of at least one of the following criteria within a period of 12 months (criteria must never have met criteria for substance dependence for the class of substance judged): Recurrent use resulting in failure to fulfill major role obligation at work, home or school; recurrent use in physically hazardous situations; recurrent substance related legal problems; and continued use despite persistent or recurrent social or interpersonal problems caused or exacerbated by substance.

In using the DSM-IV criteria, the clinician should specify whether substance dependence is with physiologic dependence (i.e., there is evidence of tolerance or withdrawal) or without physiologic dependence (i.e., no evidence of tolerance or withdrawal). In addition, patients may be variously classified as currently manifesting a pattern of abuse or dependence or as in remission. Those in remission can be divided into four subtypes—full, early partial, sustained, and sustained partial—on the basis of whether any of the criteria for abuse or dependence have been met and over what time frame. The remission category can also be used for patients receiving agonist therapy (e.g., methadone maintenance) or for those living in a controlled drug-free environment.

The term "opioid" is known in the art to relate to a psychoactive chemical targeting, e.g. binding to opioid receptors and is used accordingly in relation to the invention. These psychoactive chemicals are not limited to natural alkaloids as found, e.g., in the resin of the opium poppy, which are termed "opiates". In other words, the chemicals subsumable under the term "opioid" comprise the chemicals subsumable under the term "opiate". Opioids can, e.g., be classified into i) natural opiates (such as, e.g., morphine, codeine, thebaine, oripavine or salvinorin A), ii) esters of morphine opiates (such as e.g., diacetylmorphine (heroine), nicomorphine, dipropanoylmorphine, desomorphine, acetylpropionylmorphine, dibenzoylmorphine or diacetyldihydromorphine); iii) semi-synthetic opioids created from either the natural opiates or morphine esters (such as, e.g., hydromorphone, hydrocodone, oxycodone, oxymorphone, ethylmorphine or buprenorphine); iv) synthetic opioids (such as, e.g., fentanyl, pethidine, levorphanol, methadone, tramadol or dextropropoxyphene); and v) endogenous opioids (such as, e.g., endorphins, enkephalins, dynorphins, morphine and endomorphins). As such, the term "opioid" can be replaced by any of the above-referenced substances or substance classes falling under said term. Accordingly, abusive behavior involving the above substances or substance classes and symptoms occurring during withdrawal of the latter in a subject can now be successfully treated.

In accordance with the invention, the "treatment of symptoms" of alcohol and/or opioid withdrawal is meant to refer to the amelioration or diminishment, preferably abolition, of the symptoms associated with withdrawal of alcohol and/or opioids. As most of said symptoms per se can be classified as medical condition or disease the term "treatment" with regard to symptoms is used. As such, the invention also relates to the pharmaceutical composition of the invention for use in treating opioid and/or alcohol withdrawal.

The symptoms of alcohol withdrawal are known in the art and are triggered upon reduction or stop of alcohol consumption after prolonged periods of excessive alcohol intake. The withdrawal syndrome is largely due to the central nervous system being in a hyper-excitable state (CNS hyperexcitability; (Saitz et al., JAMA., 272(7):519-23 (1994)). The severity of the alcohol withdrawal syndrome can vary from mild symptoms such as mild sleep disturbances and mild anxiety to very severe and life threatening including delirium, particularly visual hallucinations in severe cases and convulsions (which may result in death). These symptoms appear characteristically on waking, due to the fall in the blood alcohol concentration during sleep. The severity of alcohol withdrawal depends on various factors including age, genetics, and, most importantly, degree of alcohol intake and length of time the individual has been using alcohol and number of previous detoxifications. Symptoms include, e.g., agitation, alcoholic hallucinosis, anorexia, anxiety, panic attacks, catatonia, confusion, delirium tremens, depersonalization, depression, derealization, diaphoresis, diarrhea, euphoria, fear, gastrointestinal upset, headache, hypertension, hyperthermia, insomnia, irritability, migraines, nausea and vomiting, palpitations, psychosis, rebound REM sleep, restlessness, seizures and death, sweating, tachycardia, tremors, and/or weakness. These symptoms arise when a subject that suffers from the condition of alcohol dependency is prevented from the intake of alcohol.

The symptoms of opioid withdrawal are known in the art (see, e.g., Dansou et al., Rev Prat., 62(6):837-41 (2012)). Physical symptoms include, e.g., tremors, cramps, muscle and bone pain, chills, perspiration, priapism, tachycardia, itch, restless legs syndrome, flu-like symptoms, rhinitis, yawning, sneezing, vomiting, diarrhea, weakness and/or akathisia; whereas psychological symptoms can include, e.g., dysphoria, malaise, cravings, anxiety, panic attacks, paranoia, insomnia, dizziness, nausea, and/or depression.

These symptoms arise when a subject that suffers from the condition of opioid dependence is prevented from administering him- or herself opioids.

In a preferred embodiment of the composition for use of the invention, said composition is to be administered at a dose of about 18.5 to about 77.5 mg/kg per day.

The dose to be administered as defined in this embodiment, particularly in relation to the preferred embodiments of the composition of the invention, i.e., those providing specific extract ratios, has been shown to bring about the desired treatment effects in a way particularly acceptable for both clinician and patient. As such, also envisaged are dosages of about 20 to 75 mg/kg per day such as 25 to 70, 30 to 70, 35 to 70, 40 to 65, 45 to 60 or 50 to 60 mg/kg per day. More preferred are doses of about (for each value) 50, 55, 60 or 65 mg/kg per day, and most preferred 50 mg/kg per day.

As mentioned herein above, the dose of a drug is generally adjusted by the attending physician depending on a variety of factors. As such and in dependence, for example, of the chosen concentration of the extracts of the composition upon administration, a larger amount of the composition of the invention can be administered exceeding the above mentioned range of 77.5 mg/kg a day by more than 2.5 mg such as more than (for each value) 5 mg, 7.5, 10, 15, 20, 25 or more than 50 mg. As guidance for dosing, the total daily dose should not exceed 60 mg of a composition with an average drug extract ratio of 5:1 with about 20% non-active additives.

In accordance with the invention, the compositions of the invention comprising said extract of a) with a drug-extract ratio of 4-7.5:1, said extract of b) with a drug-extract ratio of 3-8:1, said extract of c) with a drug-extract ratio of 5-7:1 and said extract of d) with a drug-extract ratio of 0.5-5:1 being present in the composition at a ratio of about 0.5 to about 4, preferably about 2.5 parts of said extract of a), about 2.5 to about 3, preferably about 3 parts of said extract of b), about 2.5 to about 5.25, preferably about 2.5 parts of said extract of c) and about 0.5 to about 3.75 parts of said extract of d) are administered at a dose of 20 to 70, more preferred 20 to 60, even more preferred 20 to 40 and most preferred 25 to 30 mg/kg per day. Also envisaged are doses of 10 to 20 mg/kg per day, 10 to 15 mg/kg per day and 15 to 20 mg/kg per day.

For example, 600 mg (300 mg *Raphanus* extract (preferably with a drug-extract ration of 3:1), 180 mg *Theobroma* extract (preferably with a drug-extract ration of 5:1), 60 mg *Passiflora* extract (preferably with a drug-extract ration of 5:1) and 60 mg *Crocus* extract (preferably with a drug-extract ration of 4:1)) of the preferred inventive composition can be administered three times daily, preferably after meals, alone or in combination with any of the additives described herein. Preferably, daily administration of the latter dose continues for 4 to 6 weeks.

In a more preferred embodiment of the composition for use of the invention, said dose is to be administered for at least two weeks.

The treatment period as defined in this embodiment, particularly in relation to the preferred embodiments of the composition of the invention, i.e., those providing specific extract ratios, has been shown to bring about the desired treatment effects in a way particularly acceptable for both clinician and patient. However, also envisaged are treatment periods of at least (for each value) 7, 8, 9, 10, 11, 12, 13 days or at least 17 days, 3 weeks, 4 weeks or at least 5 weeks or more. Conceivably, and as mentioned herein above, the dose as well as treatment period of a drug is generally adjusted by the attending physician depending on a variety of factors. As such and in dependence, for example, of the chosen concentration of the extracts within the composition when administered, a longer treatment period, e.g. when using low extract concentrations, can be an advisable and efficient strategy to achieve the desired treatment effect. Also, treatment periods can vary on the basis of a perceived level of dependence on or abuse of alcohol and/or opioids: generally, the lesser said perceived level, the lesser the administration period. In most cases of opioid and/or alcohol abuse or dependency, administration of the compositions as defined herein above, in particular in the dosages mentioned above, for at least two to four weeks is sufficient for treatment. Preferably, alcohol abuse or dependency is treated by administration of the composition of the invention for at least about 20 days, more preferred at least 25 such as 30 days.

In accordance with the invention, and preferably in relation to compositions of the invention comprising said extract of a) with a drug-extract ratio of 4-7.5:1, said extract of b) with a drug-extract ratio of 3-8:1, said extract of c) with a drug-extract ratio of 5-7:1 and said extract of d) with a drug-extract ratio of 0.5-5:1 being present in the composition at a ratio of about 0.5 to about 4, preferably about 2.5 parts of said extract of a), about 2.5 to about 3, preferably about 3 parts of said extract of b), about 2.5 to about 5.25, preferably about 2.5 parts of said extract of c) and about 0.5 to about 3.75 parts of said extract of d) and being administered at a dose of 20 to 70, more preferred 20 to 60, even more preferred 20 to 40 and most preferred 25 to 30 mg/kg per day, said administration is maintained for at least (for each value) 7, 8, 9, 10, 11, 12, 13, 14 days or at least 17 days, 3 weeks, 4 weeks or at least 5 weeks.

In another embodiment, the invention relates to a method for producing a composition comprising an extract of a plant belonging to the genus *Raphanus* and an extract of a plant belonging to the genus *Theobroma*, comprising the steps of: a) extracting at least air roots, seeds and/or bulbs of the *Raphanus* plant with a hydrophilic, medium-polar and/or lipophilic solvent; b) extracting at least the fruit of the *Theobroma* plant with a hydrophilic and/or medium-polar solvent; and c) combining the extract of step a) with the extract of step b), thereby producing said composition comprising an extract of a plant belonging to the genus *Raphanus* and an extract of a plant belonging to the genus *Theobroma*.

The definitions, combinations and specific parameters for the extraction referred to herein above also apply mutatis mutandis to this embodiment and its preferred modifications referred to herein below.

In a preferred embodiment of the method of the invention, the method comprises the further steps of d) extracting at least the flower of a plant belonging to the genus *Passiflora* with a hydrophilic, medium-polar and/or lipophilic solvent; and/or e) extracting at least the flower of a plant belonging to the genus *Crocus* with a hydrophilic, medium-polar and/or lipophilic solvent, prior to step c), in which case the extract of step d) and/or the extract of step e) is/are combined with said extracts of step a) and step b); or after step c), in which case the extract of step d) and/or the extract of step e) is/are combined in a further step f) with the composition of step c), thereby producing a composition comprising an extract of a plant of the genus *Raphanus*, an extract of a plant of the genus *Theobroma*, an extract of a plant of the genus *Passiflora* and/or an extract of a plant of the genus *Crocus*.

As mentioned herein above, in a further preferred embodiment of the composition of the invention, the composition for use of the invention or the method of the invention, the plant belonging to the genus *Raphanus* is a *Raphanus sativus* plant; and/or the plant belonging to the genus *Theobroma* is a *Theobroma cacao* plant.

The single extracts as well as combinations thereof such as those forming the composition of the invention as described herein above are preferably stored in sealed containers and protected from sunlight either by storage in dark places or in containers that block light from entering said containers, preferably, at temperatures of 4 to 8° C. Preferably, the containers are sealed airtight and oxygen free. Combination of the extracts is preferably performed in dried state of each extract. The minimum shelf life is expected to be 2 years for fluid (e.g., alcoholic) extracts and at least 3 years for dried extracts.

In an additional preferred embodiment of the composition of the invention as also mentioned above, the composition for use of the invention or the method of the invention, the plant belonging to the genus *Passiflora* is a *Passiflora incarnata* plant; and/or the plant belonging to the genus *Crocus* is a *Crocus sativus* plant.

Plants from the species *Raphanus sativus, Theobroma cacao, Passiflora incarnata* and *Crocus sativus* are particularly preferred plants from which the extracts forming the composition of the invention can be obtained and whose extracts have been used in the compositions exemplified herein below.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply mutatis mutandis to all attached claims.

The figures show:

FIG. 1:

Dose—response effect of orally administered extract composition on the intraperitoneal administration of morphine or heroine to re-establish motor behavior in rats. Each data point represents the mean (±SD) of five rats. * Significant differences between baseline and each treatment $p<0.001$; † significant difference between that dose to its lesser dose ($p<0.001$).

FIG. 2:

% Dependence reduction to morphine or heroin following oral administration of extract composition. Each data point represents the mean (±SD) of five rats. * Significant differences between baseline and each treatment $p<0.001$; † significant difference between that dose to its lesser dose ($p<0.001$).

FIG. 3:

HIC score for mice exposed for 72 h of ethanol. Mice were treated at 1 and 4 h with different doses of the extract or vehicle and the HIC scores were recorded overtime for 64 h. HIC scores were significantly less ($p<0.001$) in 40 or 60 mg/kg extract treated groups for the first 12 h.

FIG. 4:

Brief spindle episodes (BSE) activities were recorded in mice following chronic exposure to ethanol. Mice treated with 40 and 60 mg/kg of the extract composition have significantly less BSE from 2 to 72 h following ethanol withdrawal than vehicle treated mice. The BSE activities for mice treated with 40 or 60 mg/kg of the extract composition were significantly less ($p<0.001$) than vehicle treated mice.

The examples illustrate the invention:

EXAMPLE 1: SELF-ADMINISTRATION MODEL 1.1 Material and Methods
1.1.1 Extract Composition The extract composition used in example 1 and all other examples was made up as follows:
- 2.5 parts of a *Raphanus sativus* extract, said extract being obtained by extraction as follows:
  - Adding 500 ml of 30% methanol/water mixture to 90 g dried powdered radish in a glass beaker
  - Heating solution to 40 to 50° C. for 30 min
  - Filtering solution and evaporating filtrate under vacuum to dryness
  - Freeze-drying the dried residue for 24 hrs (the resulting native extract quantity was 36.3 g dried extract)
  - Adding 40% excipients (37 parts maltodextrin and 3 parts silica) for standardization purposes so that the extract is standardized to contain at least 1.5% total flavonoids
- 3 parts of a *Theobroma cocoa* extract, said extract being obtained by extraction as follows:
  - Adding 1 Liter purified water to 200 g of dried powdered cacao fruits in a glass beaker
  - Heating solution between 70-80° C. for 45 min.
  - Filtering solution and evaporating the filtrate to a volume of 100 mL
  - Freezing and freeze drying for 24 hours.
  - Adding excipients to standardize the extract to contain a min. concentration of procyanidins.
- 2.5 parts of a *Passiflora incarnata* extract, said extract being obtained by extraction as follows:
  - Adding 750 mL methanol to 175 g of dried powdered passion flowers in a glass beaker
  - Heating solution between 40-50° C. for 30 min.
  - Filtering solution and evaporating to dryness.
  - Freeze drying the residue for 24 hours.
  - Adding excipients to standardize the extract to contain a min. concentration of flavonoids.
- 1.5 parts of a *Crocus sativus* extract, said extract being obtained by extraction as follows:
  - Adding 300 mL ethanol to 10 g of dried powdered saffron flowers in a glass beaker
  - Heating solution between 30-45° C. for 30 min.
  - Filtering solution and evaporating to dryness.
  - Freeze drying the residue for 24 hours.
  - Adding excipients to standardize the extract to contain a min. concentration of safranal.

The dried extracts were mixed in a mixture of water and olive oil.

1.1.2 The Intravenous Self-Administration Apparatus

Responses on either of two levers (mounted 15 cm apart on the front wall of each operant test cage) were recorded on an IBM compatible computer with a Med Associates interface. The intravenous self-administration system consisted of polyethylene silicone cannulas con-structed according to the design of Weeks (1972) (Weeks J R. Long-term intravenous infusion. In: Myers R D, editor. Methods in Psychobiology. Vol. 2. Academic Press; New York: 1972. pp. 155-168), Instech harnesses and swivels, and Harvard Apparatus infusion pumps. Shaping of the bar-press response was initially accomplished by training rats to bar-press for water. Cannulas were then implanted in the external jugular vein according to procedures described by Weeks (1972) (see above). Self-administration testing began with a 16-h nocturnal session followed by daily 1-h sessions, 6 days a week. A lever-press response produced a 10-ml infusion of drug solution (0.01 mg of morphine sulfate) in about 0.2 s or a 50-ml infusion of drug solution.

1.1.3 The Plus Maze Procedure

The apparatus was made of black Plexiglas and consisted of two runways that intersected at the center at right angles. Each arm of the maze measured 40×10 cm (length by width). Two of the arms that were opposed to each other had walls that measured 40 cm in height (closed arms), whereas the other two arms had no walls (closed arms). The maze was elevated 52 cm above the floor. It was located in a darkened room so that only the open arms were illuminated, each with its own 40-W incandescent light. Animals were placed in the center of the maze and the number of entries into each type of arm was counted (all four paws in the arm defining an entry) as was the time spent on each type of arm. The test was terminated 5 min after the animal was placed in the center. The following measures were calculated: total number of arm entries, entries into open and closed arms, time in open and closed arms, and percent of total time spent in open arms. Changes in the total number of arm entries reflect a general index of activity, whereas changes in the percent measure constitute an index of anxiety. Increased percent open-arm time reflects an anxiolytic state, while decreased percent open-arm time reflects an anxiogenic state. Animals' movements were recorded by using an overhead video camera and VCR. They were subsequently scored by a "blind" observer.

1.1.4 Microdialysis Study

Under pentobarbital anesthesia (50 mg/kg ip), the rats were implanted stereotaxically with a microdialysis guide cannula (CMA: 8309010; Acton, Mass.) over the nucleus accumbens and with bilateral injector guides 0.5 mm above the interpeduncular (Paxinos and Watson, 1986, The rat brain in stereotaxic coordinates, Ed 2. (Academic Press, London)). Animals were monitored for proper recovery but otherwise left undisturbed for 4 days after surgery. The afternoon prior to the in vivo microdialysis experiment, the rats were placed in a cubical microdialysis chamber with free access to food and water. With the rats briefly anesthetized with Brevital (45 mg/kg ip), dialysis probes were inserted through the guide cannulas. Artificial cerebrospinal fluid containing 146 mM NaCl, 2.7 mM KCl, 1.2 mM $CaCl_2$, and 1.0 mM $MgCl_2$ was delivered continuously by a Harvard syringe pump at a flow rate of 1 ml/min. Collection of perfusates began the next day. Twenty-minute fractions were collected in vials containing 2.0 ml of 1.1 M perchloric acid solution (containing 50 mg/l EDTA and 50 mg/l sodium metabisulfite). After 2 h of baseline collections, 18-MC (10 mg) or vehicle was locally administered into the interpeduncular nucleus and the rats received a dose of morphine (5 mg/kg ip) or saline. The collection of dialysate samples was then continued for 3 h. Upon completion of an experiment, rats were killed by an overdose of pentobarbital. Each brain was removed, frozen, and sliced in a cryostat. The tracks left by the probes were identified and their exact positions determined by reference to the atlas of Paxinos and Watson (1986) (The rat brain in stereotaxic coordinates, Ed 2. (Academic Press, London)).

Dialysate samples were assayed for dopamine, dihydroxyphenylacetic acid (DOPAC), and homovanillic acid (HVA) by high-pressure liquid chromatography (HPLC) with elec-trochemical detection. The HPLC system consisted of an ESA autosampler, an ESA solvent delivery system, an C18 column. The mobile phase consisted of 0.075 mM sodium dihy-drogen phosphate, monohydrate, 0.0017 mM octane sulfonic acid, and 25 mM EDTA in 10% HPLC grade acetonitrile, adjusted to pH 3.0 with phosphoric acid. The flow rate was set at 0.53 ml/min.

1.1.5 Microinjection Study

Rats were stereotaxically implanted under sodium pentobarbital anesthesia (50 mg/kg) with bilateral gauge injector guides (Plastics One, Roanoke, Va., USA) 0.5 mm above the interpeduncular nuclei (Paxinos and Watson, 1986, see above). Obturators were screwed into the injector guides. The injector guides were fastened to the skull using stainless steel screws and cranioplastic cement. Rats were returned to individual cages and were provided with food and water ad libitum. The cages were kept on a heating pad overnight, and the following day the rats were returned to the colony room. Rats were allowed at least 4-5 days of recovery from surgery before being utilized in microinjection studies. Morphine and extract composition (or vehicle) were locally administered into the interpeduncular nucleus using an infusion pump (Harvard Apparatus); all such treatments were administered in a 1-ml volume during a 1-min infusion to prevent reflux through the guide cannula; the injection cannula was kept in place for an additional minute after a treatment was administered.

1.2 Results

The extract composition reduced the self-administration of morphine abuse; at 40 mg/kg, these effects generally lasted for 18-64 h. The extract mixture (40 mg/kg) appeared to produce downward shifts, without any displacement to the left or right, in the entire unit infusion dose—response curve of a self-administered drug, indicating that reinforcing efficacy was reduced (i.e., morphine and other drugs of abuse like nicotine were less reinforcing in the presence of the extract composition). It should also be noted that the extract mixture was potent at reducing self-administration. The extract mixture showed very good activity on the opium receptors.

EXAMPLE 2: MOTOR BEHAVIOUR TEST 2.1 Material and Methods

Rats weighing 250 g±10% were utilized in the experiment. Each group consisted of 5 animals.

The rotarod performance test is the test used herein to assess the motor coordination of rats following the induction of dependence on morphine or heroin. Rat's response is delivered following administration of 0.04 mg/kg of morphine, 0.04 mg/kg of heroin following a 10-ml infusion of drug solution (0.01 mg of morphine sulfate) in about 0.2 s or a 50-ml infusion of drug solution (0.015 mg of heroin sulfate) in the same concentration.

To assess the effects of experimental treatments, experiments were performed when baseline of administration rates stabilized within 10% variation from one day to the next 5 days. This took 20 days of testing to show dependence and consistent motor performance using the rotarod performance test. Morphine or heroin i.p. doses were administered daily into rats to equilibrate behavior. Following the oral administration of extract, the doses of morphine or heroin were adjusted to equilibrate the motor coordination similar to the "normal" condition.

Performance measures of motor behavior were conducted using a commercially designed and constructed accelerating rotarod (Rotamex). Motor coordination was quantified as the animal's ability to remain in place on an accelerating rotating rod. Before drug dosing, rats were gradually trained to stay on the rod by providing them six to eight 3-min training periods per day. The rats were trained at increasing rod speeds of 3, 6, 9, 12, and 15 rpm for periods of 3 min. Electric shock (2 mA, AC) was present on the apparatus floor to encourage the animal to stay on the rod. The animal's time of falling was recorded automatically by photocell detection. An individual animal was considered trained when it reached a criterion of two successive trials at 15 rpm wherein it stayed on the rod for the full 3-min session. Only those rats that met this criterion after 2 days of training were used in these experiments. All testing was conducted at least 2 h after the final training trial. Drugs were given by intraperitoneal injection 30 min prior to the testing session. Animals were placed on the rod while it was rotating at 10 rpm. Upon placement, the rod's rotational speed was increased at a rate of 8.3 rpm/min. Total possible test session duration was 3 min. Time of falling and revolutions per minute at time of fall were recorded for each animal.

All data were presented as a mean±standard deviation (SS) as either mg/Kg or % and assessed by using one way ANOVA analysis followed by a post hoc test (Tukey's test) (95% confidence) for multiple comparisons (SPSS version 17). P value less than 0.05 (<0.05) is considered statistically significant.

2.2 Results and Conclusions

Figure 2:
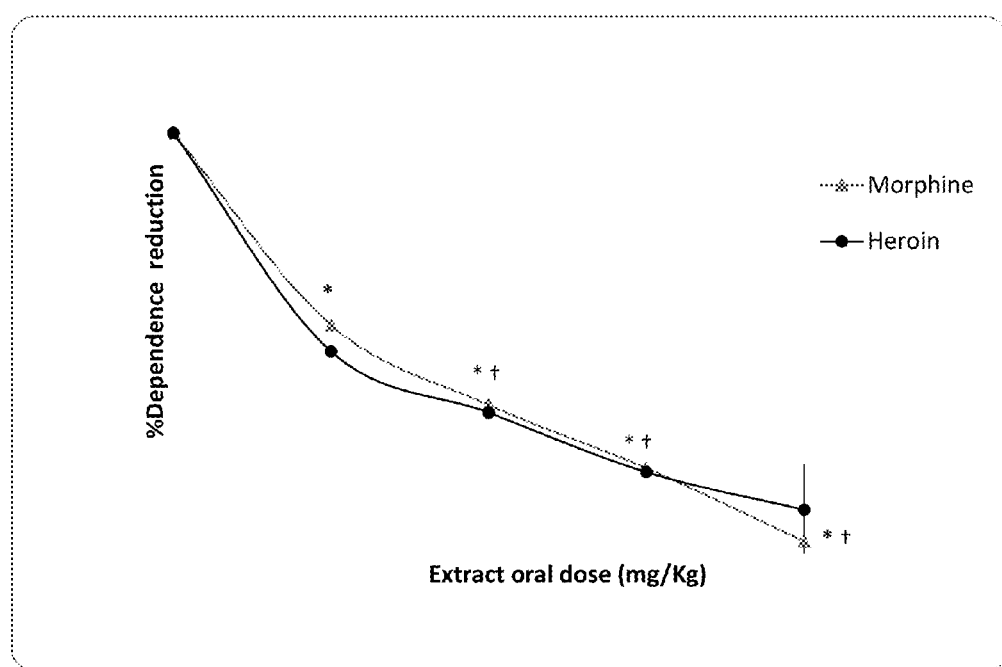

Increasing doses of extract composition administration reduced significantly (p<0.001) the doses of morphine and heroin in order to stabilize rats motor coordination according to the rotarod performance test (FIG. 1). This latter effect was dose-dependent and the percentage of reduction of morphine or heroin was reduced significantly with higher doses (FIG. 2). The 50% dependency reduction values were 9.8 and 12.5 mg/kg for heroin and morphine respectively (FIG. 2). The results indicate that the extract reduced morphine and heroin dependence in dose-dependent manner but without showing superiority of either of the opioid narcotics used.

EXAMPLE 3: CNS HYPER EXCITABILITY ASSOCIATED WITH ALCOHOL WITHDRAWAL IN A MOUSE MODEL OF Ethanol Dependence 3.1 Materials and Methods Animals Adult male mice (80-90 days of age) were used in these experiments. The mice weighed 25-30 g at the start of the experiments.

Extract Preparation and Administration

Extract composition was dissolved in saline, and saline alone was used as the vehicle. Extract composition was administered orally.

Ethanol Exposure and Measurement

Mice were chronically exposed to ethanol vapor in Plexiglas inhalation chambers (60×36×60 $cm^3$). Briefly, ethanol (95%) was volatilized by passing air through an air stone submerged in ethanol. The ethanol vapor was mixed with fresh air and delivered to the chambers at a rate of 10 l/min, which maintained the ethanol concentration in the chamber in the range of 10-13 mg/L air. Prior to entry into the ethanol chambers, intoxication was initiated by administration of ethanol (1.6 g/kg; 8% w/v; ip.) and blood ethanol concentration (BEC) was stabilized by administration of the alcohol dehydrogenase inhibitor, pyrazole (1 mmol/kg). Mice maintained in the control (air) chamber received injections of saline and pyrazole. The housing conditions in the inhalation chambers were identical to that in the colony room. Immediately after removing mice from the inhalation chambers, blood samples were collected for determination of BEC. Chamber ethanol concentration was determined daily by collecting air samples (2 ml) with a gas-tight syringe through a port in the chamber wall. The samples were then transferred to Venoject™ tubes for later analysis using an enzymatic spectrophotometric assay procedure. Ethanol concentration in the chambers is expressed as mg/L air. Blood samples were collected from the retro-orbital sinus with heparinized capillary tubes. The samples were centrifuged for phase separation and 5 µl of plasma were injected into an Analox Instrument analyzer (Lunenburg, Mass.). BEC (in mg/dl) was recorded by measuring oxygen uptake generated by the oxidation of ethanol to acetaldehyde and hydrogen peroxide by ethanol oxidase.

Handling-Induced Convulsion (HIC)

Mice were randomly assigned to ethanol treatment conditions and then separated into several groups (control and concentration-dependent groups). Mice were continuously exposed for 72 h to ethanol vapor in inhalation chambers. Upon removal from the inhalation chambers, blood samples were collected for determining blood ethanol concentration (BEC). At 1 and 4 h following ethanol withdrawal, mice received oral administration of the extract composition (0, 20, 40 or 60 mg/kg). The convulsions induced following withdrawal of alcohol were recorded as handling-induced convulsion (HIC) response. HIC response has proven to be a sensitive and reliable index of CNS hyper-excitability associated with ethanol withdrawal.

Electroencephalographic Activity

Separate groups of mice were used to assess electrographic measures of ethanol withdrawal. Mice were stereotaxically implanted with chronic indwelling electrodes, as previously described. Briefly, monopolar stainless steel, semi-micro electrodes (120 mm) were implanted into hippocampus (AP: −1.65 mm; L: 1.5 mm; V: −2.25 mm), amygdala (AP: −0.7 mm; L: −2.25 mm; V: −5.25 mm), and visual cortex (AP: −3.0 mm; L: −2.0 mm), along with a stainless steel screw in the nasal area (AP: +4.0 mm; L: +0.5 mm) for use as a reference electrode. The coordinates are given relative to bregma. Electrodes were connected to a four-pin MicroTech plug and fixed to the skull using dental acrylic and a light-cured resin composite. Three to five days following the surgery, baseline electroencephalographic (EEG) activity was recorded from freely moving mice every 2 h over an 8 h period. The next day, mice were placed in the inhalation chambers and received 72 h continuous exposure to ethanol vapor. At 1 and 4 h following ethanol withdrawal, mice received orally the extract composition (0, 40 or 60 mg/kg). EEG data were collected during withdrawal with additional samples recorded at 24, 32, 48, and 72 h post-withdrawal. Recording sessions were conducted in electrically-shielded chambers, with electrode cables connected to Grass amplifiers. Spontaneous EEG data were digitized by a CED analog-to-digital converter and trains of high-voltage electrographic activity, known as brief spindling episodes (BSE), were identified by a computer program (Spike2). Briefly, automated analysis entailed identifying and classifying bursts of EEG activity with a frequency between 7 and 9 Hz and duration of at least 1 s. Data are presented as percent BSE activity (i.e. cumulative duration of all BSE events relative to entire duration of each recording session).

Data Analysis

Data was presented as HIC scores or BSE activity and the data between groups were analyzed by analysis of variance (ANOVA) followed by a post-hoc test. P<0.05 was considered significant.

3.2 Results

Figure 3:
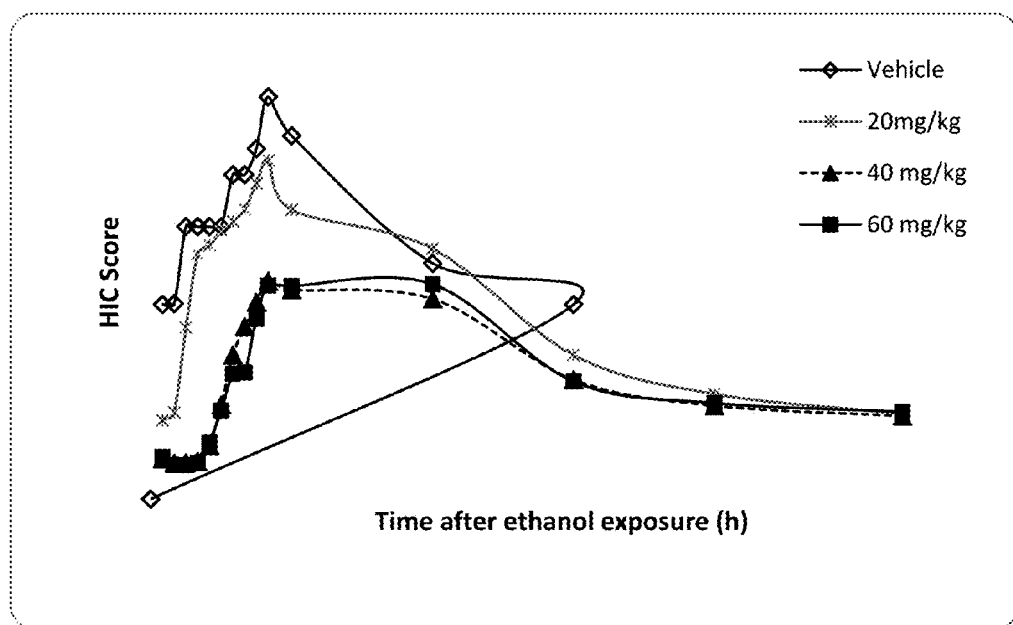
Figure 4:
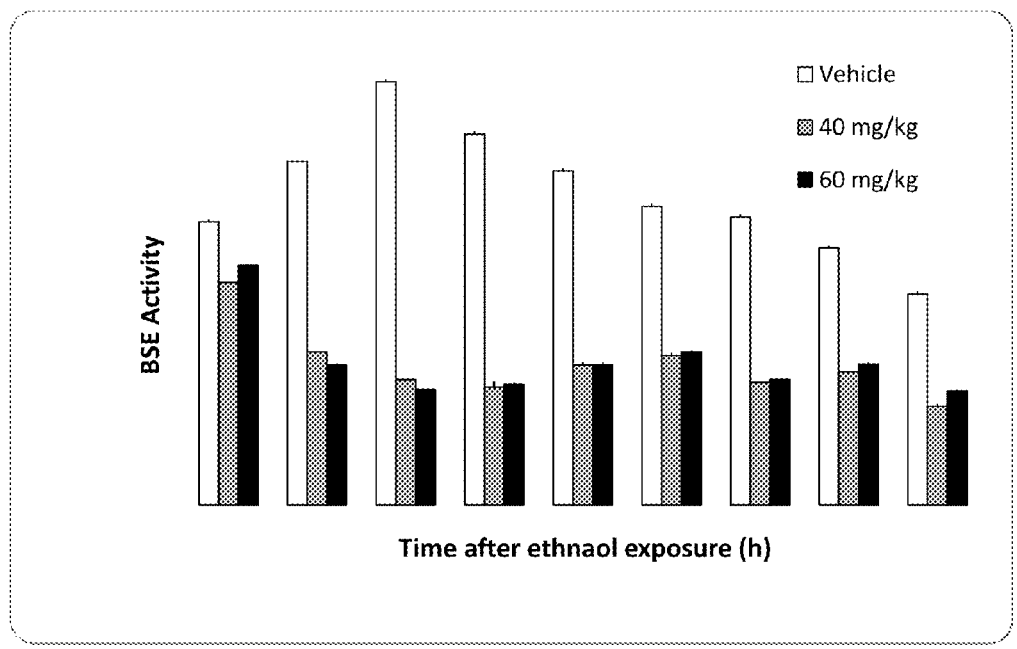

Extract composition was administered at 1 and 4 h following ethanol withdrawal. The extract at 40 and 60 mg/kg doses reduced significantly (P<0.001) HIC scores in comparison to vehicle treated mice (FIG. 3). This reduction was observed during the first 12 h post withdrawal. The 20 mg/kg extract dose exhibited a pattern of reduction in HIC scores; however, they were not significant. Furthermore, there were no differences in HIC scores between 40 and 60 mg/kg treated groups (FIG. 3). Similarly, the extract composition at 40 or 60 mg/kg reduced significantly the BSE activity in a time dependent fashion (FIG. 4). The maximum reduction in BSE activities were observed during the first 36 h post alcohol withdrawal. After 36 h however, the BSE activity in the vehicle-treated group started to decline. Finally, the extract composition treatment of repeated withdrawals was effective in blocking the development of withdrawal sensitization observed in vehicle-treated mice.

EXAMPLE 4: TREATMENT OF ALCOHOL DEPENDENCE IN PATIENTS WITH DEPRESSIVE DISORDER

The extract composition has serotonin re-uptake inhibitors factors. Thus, alcohol-dependent patients with co-morbid major depressive disorder were compared.
4.1 Methods
Four alcohol-dependent patients comorbid with major depressive disorder in municipal alcohol clinics were given the extract composition (40 mg/kg) in a small pilot study. During the 6-week study period patients continued their routine treatment at the clinics. Abstinence was not required but encouraged. The patients attended visits weekly during the first two weeks, and then at 4 and at 6 weeks. Outcome measures were Alcohol Use Disorders Identification Test (AUDIT), Obsessive Compulsive Drinking Scale (OCDS) and Drinking Diary.
4.2 Study Participants
Three men and one woman aged 31 to 47 years who were voluntarily seeking outpatient treatment for alcohol problems at two Jordanian municipal alcohol-clinics. Patients with a history of heavy drinking (averaging four or more daily drinks for men and three or more daily drinks for the women) for at least five years, significant depression defined by the Beck Depression Inventory II (BDI-II>16), and who were interested in voluntarily taking part in the study were recommended by their clinic doctor to be screened by the study physician. The patients were interviewed by the study doctor (psychiatrist LM) applying the Structured. The time since the last prior inpatient detoxification had to be at least four weeks. In addition, the eligible patients had to be currently in a depressive episode lasting for more than two weeks. The exclusion criteria included other substance use dependence screened by urine test (amphetamine, benzodiazepines, cocaine, tetrahydrocannabinol and opiates) schizophrenia or other psychotic disorder, and bipolar I and II disorder, acute risk of suicide, pregnancy or breastfeeding, a severe untreated somatic problem, or a serious dysfunction of the liver and mental disability. Other medications prescribed by participants' physicians were allowed, with the exception of other antidepressants. All patients were Jordanian. The mean length of the present depressive period was 22 months. Informed consent was obtained from all patients participating in the study.
4.3 Study Design
Four patients were initially screened. A screening interview (SCID) was conducted to confirm the diagnoses of MDD and alcohol dependence. Patients completed questionnaires including the Obsessive-Compulsive Drinking Scale (OCDS; Anton R F: Obsessive compulsive aspects of craving: development of the Obsessive Compulsive Drinking Scale, Addiction 2000, 95: (211-217)) and the Alcohol Use Disorders Identification Test (AUDIT; Saunders J B et al., 1993, Development of the alcohol Use disorders identification test (AUDIT): WHO collaborative project on early detection of persons with harmful alcohol consumtion II, Addition 1993, 88(6):791-804), AUDIT-QF (Aalto M et al., 2006, Alcohol Clin Exp. Res., effectiveness of structured questionnaires for screening heavy drinking in middle aged women, 30(11): 1884-1888), and AUDIT-3 (Gual A et al., 2002, Alcohol (37(6):591-596, Audit-3 and Audit-4: effectiveness of two short forms of the alcohol) were used for a detailed drinking analysis. The recording of alcohol use disorders identification test, consumption during the 6-week treatment period was done with a personal drinking diary for all days.

Eligible patients received orally 40 mg/day extract composition. Patients were instructed to take the study medication in the morning. Patients were permitted to telephone the study physician at any time. If the patient did not appear at a scheduled visit, a new appointment was offered.

During the 6-week treatment period, the patients returned to the study site at weeks 2, 4±2, and 6±2 for data collection and for medication checking and dispensing. At each visit, the drinking diary and the study medication intake since the previous visit were recorded from the medication diary. The study medication was ensured by pill count from the returned used bottle. Outcomes were recorded on specific weeks: OCDS (weeks 0, 2, 4 and 6); AUDIT (week 0, 2 and 6). Clinical laboratory tests (MCV, AST, ALT, CDT, and GGT) were taken at the beginning of the study and were repeated at weeks 2, 4, and 6, to ensure the safety of the medication. No breath or blood test for alcohol was performed, but if the patient was obviously intoxicated, a new appointment was offered.
Statistical Analysis
All primary and secondary outcome statistical analysis was performed by an independent source.
4.4 Results
The baseline AUDIT and alcohol use histories are similar in AUDIT scores decreased from baseline, from 27.6±6.3 to 12.47±7.9 in the extract composition group (40 mg/kg). The overall reduction was highly significant ($p<0.0001$).

Alcohol consumption measured by the AUDIT QF (quantity-frequency) score was significantly reduced: extract composition (40 mg/kg) from 6.1±1.4 to 3.7±2.3 and from 6.0±1.5 to 4.1±2.1 ($p<0.0001$). The treatment by time interaction was not significant. The number of heavy drinking days measured by the AUDIT-3 score was also diminished significantly: for the 40 mg extract mixture/kg from 2.7±0.9 to 1.6±1.1 and from 3.0±0.8 to 2.2±1.1 ($p>0.0001$). The treatment by time interaction was not significant.
4.5. Results Summary
Alcohol consumption measured by the AUDIT QF (quantity-frequency) score was significantly reduced with these people to whom the extract composition was given.

EXAMPLE 5: EXTRACT OF *RAPHANUS* INCREASES BRAIN DOPAMINE CONCENTRATIONS IN RATS

Materials and Methods
2.1. Experimental Animals
Male Wistar rats (250-300 g, Amman-Jordan) were used throughout the study (8 rats for each experiment). Animals were housed in groups of 4/cage in a 12/12 h light-cycle (lights on at 07.00 a.m.), with ad-lib food and water available. The animals were randomly allocated to different groups of the experiment. All experiments were conducted in accordance with standard ethical guidelines and approved by the local ethical Committee University of Medical Committee on the Use and Care of Animals, 81/021, Jul. 10, 2011 (Petra University, Amman, Jordan)).
2.2. Drugs
Fluoxetine hydrochloride [N-methyl-3-[(4-trifluoromethyl) phenoxy]-3-phenylpropylamine hydrochloride] and desipramine hydrochloride [10-11-dihydro-N-methyl-5H-dibenz (Z) [b, f] azepine-5-propanamine hydrochloride]

(TOCRIS Bioscience, UK) were dissolved in sterile saline and administered intraperitoneally at a concentration of 1 ml/kg; the extract was prepared immediately before use. The control groups were administered saline.

2.3. Plant Material

The *Raphanus sativus* extract used was prepared in Jordan. To prepare the extract, 100 g of dried and milled stigma was extracted with 1000 ml distilled water by maceration. The extract was dried at 35° C.-40° C., and the yield of extraction was 23 mg of freeze-dried powder per 100 mg dry stigma. The extract was dissolved in normal saline and immediately administered to the animals.

2.4. Brain Preparation

Thirty minutes after drug and/or extract injection, animals were killed in a $CO_2$ box, beheaded by a guillotine, and their brains were removed by a specialist in less than a minute. Brains were homogenized in a Falcon tube containing 10 ml of cool (0° C.) sterile saline and centrifuged at 3000 rpm/min for 5 min at 4° C. The supernatant was used for subsequent neurotransmitter detection by ELISA. On the basis of previous studies, an interval time of 30 min was selected; this time was considered to be sufficient for extract action.

2.5. Statistical Analysis

Data are represented as means±standard error of mean (SEM) of the neurotransmitters concentration. One way analysis of variance (One-Way ANOVA) 3.

Results 3.1 Effects of *Raphanus* Extract on Brain Serotonin Concentration

The effect of different doses of *Raphanus* extract (2, 8, 32, 64, 128 and 256 mg/kg, i.p.) on brain serotonin was studied. The animals received either saline (1 ml/kg, i.p.), or fluoxetine (10 mg/kg, i.p.), desipramine (50 mg/kg, i.p.), *Raphanus* extract (different concentrations) and were sacrificed 30 min later. One way ANOVA indicated that fluoxetine can increase brain serotonin levels significantly but neither desipramine nor *Raphanus* extract can increase brain serotonin levels.

3.2 Effects of *Raphanus* Extract on Brain Dopamine Concentration

Our results indicated that both fluoxetine (10 mg/kg, i.p.) and desipramine (50 mg/kg, i.p.) can increase dopamine concentration in the brain.

Interestingly, the *Raphanus* extract can increase dopamine concentration in the brain in a dose-dependent manner with the extract dose of 256 mg/kg, i.p. being the most potent in this study.

3.3 Effects of *Raphanus* Extract on Brain Glutamate Concentration

In the last part of the experiments, the effect of the *Raphanus* extract on brain glutamate concentration was investigated. The results indicated that there were fluctuations in brain glutamate level in dependence from the doses of the extract. The extract increased the glutamate concentration in the brain significantly, e.g., using the dose of 264 mg/kg, i.p.

The invention claimed is:

1. A pharmaceutical composition for treating opioid and alcohol abuse, and/or symptoms of opioid and alcohol withdrawal comprising:
   (a) 2.5 parts of an extract of *Raphanus sativus*,
   (b) 3 parts of an extract of *Theobroma cacao*,
   (c) 2.5 parts of an extract of *Passiflora incarnata*, and
   (d) 1.5 parts of an extract of *Crocus sativus*.

2. The pharmaceutical composition of claim 1 further comprising a carrier.

3. The pharmaceutical composition of claim 2, wherein the carrier is olive oil.

4. The pharmaceutical composition of claim 3, wherein olive oil is present in the composition at a ratio of about 1 part of olive and about 4 parts of said extracts in mass.

5. The pharmaceutical composition of claim 1, wherein said extract of (a) is obtainable or obtained by extracting at least the air roots, seeds and/or bulbs with a hydrophilic, medium-polar and/or lipophilic solvent; and said extract of (b) is obtainable or obtained by extracting at least the fruit with a hydrophilic and/or medium-polar solvent; said extract of (c) is obtainable or obtained by extracting at least the flower with a hydrophilic, medium-polar and/or lipophilic solvent; and said extract of (d) is obtainable or obtained by extracting at least the flower with a hydrophilic, medium-polar and/or lipophilic solvent.

6. The pharmaceutical composition of claim 5, wherein said solvent of (a) is; and/or wherein said solvent of (b) is a water/alcohol mixture.

7. The pharmaceutical composition of claim 1, further comprising:
   (e) black cumin seed oil.

8. A method for treating opioid abuse or dependency, and/or alcohol abuse or dependency, and/or symptoms of opioid and alcohol withdrawal in a subject in need, comprising administering to the subject a pharmaceutical composition of claim 1.

9. The method of claim 8, wherein the pharmaceutical composition is administered to the subject at a dose of about 18.5 to about 77.5 mg/kg per day.

10. The method of claim 9, wherein said dose is administered for about 7 days to about 5 weeks.

11. The method of claim 10, wherein said dose is administered for at least two weeks.

12. The method of claim 8, wherein the symptoms of alcohol withdrawal include agitation, alcoholic hallucinosis, anorexia, anxiety, panic attacks, catatonia, confusion, delirium tremens, depersonalization, depression, derealization, diaphoresis, diarrhea, euphoria, fear, gastrointestinal upset, headache, hypertension, hyperthermia, insomnia, irritability, migraines, nausea and vomiting, palpitations, psychosis, rebound REM sleep, restlessness, seizures, sweating, tachycardia, tremors, and/or weakness.

13. The method of claim 8, wherein the symptoms of opioid withdrawal include tremors, cramps, muscle and bone pain, chills, perspiration, priapism, tachycardia, itch, restless legs syndrome, flu-like symptoms, rhinitis, yawning, sneezing, vomiting, diarrhea, weakness and/or akathisia; whereas psychological symptoms can include dysphoria, malaise, cravings, anxiety, panic attacks, paranoia, insomnia, dizziness, nausea, and/or depression.

14. The method of claim 8, wherein the pharmaceutical composition is administered orally.

* * * * *